United States Patent
Vulpe et al.

(10) Patent No.: US 11,932,878 B2
(45) Date of Patent: Mar. 19, 2024

(54) METABOLICALLY COMPETENT CELLS, METHODS OF MAKING, AND USES THEREOF

(71) Applicants: University of Florida Research Foundation, Inc., Gainesville, FL (US); THE RESEARCH FOUNDATION FOR THE STATE UNIVERSITY OF NEW YORK, Albany, NY (US)

(72) Inventors: Christopher Dillon Vulpe, Gainesville, FL (US); Amin Sobh, Gainesville, FL (US); David Michael Faulkner, Gainesville, FL (US); Abderrahmane Tagmount, Gainesville, FL (US); Michael Fasullo, Albany, NY (US)

(73) Assignees: University of Florida Research Foundation, Inc., Gainesville, FL (US); The Research Foundation for the State University of New York, Albany, NY (US)

( * ) Notice: Subject to any disclaimer, the term of this patent is extended or adjusted under 35 U.S.C. 154(b) by 1157 days.

(21) Appl. No.: 16/315,675

(22) PCT Filed: Jul. 7, 2017

(86) PCT No.: PCT/US2017/041202
§ 371 (c)(1),
(2) Date: Jan. 7, 2019

(87) PCT Pub. No.: WO2018/009869
PCT Pub. Date: Jan. 11, 2018

(65) Prior Publication Data
US 2019/0300861 A1    Oct. 3, 2019

Related U.S. Application Data

(60) Provisional application No. 62/359,478, filed on Jul. 7, 2016.

(51) Int. Cl.
*C12N 15/85* (2006.01)
*C12N 5/16* (2006.01)
*C12N 9/06* (2006.01)
*C12N 9/10* (2006.01)
*C12N 15/10* (2006.01)
*C12N 15/113* (2010.01)
*C12N 15/90* (2006.01)
*G01N 33/50* (2006.01)

(52) U.S. Cl.
CPC ............. *C12N 5/16* (2013.01); *C12N 9/002* (2013.01); *C12N 9/10* (2013.01); *C12N 15/1079* (2013.01); *C12N 15/113* (2013.01); *C12N 15/907* (2013.01); *G01N 33/5014* (2013.01); *C12N 2310/20* (2017.05); *C12N 2510/04* (2013.01); *C12Y 114/13073* (2013.01); *C12Y 114/13097* (2013.01); *C12Y 204/01017* (2013.01); *G01N 2500/10* (2013.01)

(58) Field of Classification Search
None
See application file for complete search history.

(56) References Cited

U.S. PATENT DOCUMENTS

2005/0130116 A1    6/2005   Dohmer et al.
2014/0377868 A1   12/2014   Joung et al.

FOREIGN PATENT DOCUMENTS

WO    2014/202627 A2    12/2014

OTHER PUBLICATIONS

Zhang et al (BioRxiv, posted online Feb. 18, 2016, pp. 1-27). (Year: 2016).*
Jover et al (FEBS, 1998, vol. 431, pp. 227-230). (Year: 1998).*
Konermann (Nature 2015, vol. 517, (7536) pp. 583-588). (Year: 2015).*
International Search Report and Written Opinion for PCT/US2017/041202 dated Sep. 22, 2017.
Aninat, et al. "Expression of Cytochromes P450, Conjugating Enzymes and Nuclear Receptors in Human Hepatoma HepaRG Cells," Drug Metabolism and Disposition, Oct. 3, 2005, vol. 34, No. 1, pp. 75-83.
Gaytan, et al. "Functional Toxicology: Tools to Advance the Future of Toxicity Testing," Frontiers in Genetics, Mar. 31, 2014, vol. 5, pp. 1-10.
Hariparsad, et al. "Comparison of Immortalized Fa2N-4 Cells and Human Hepatocytes as in Vitro Models for Cytochrome P450 Induction," Drug Metabolism and Disposition, Jun. 1, 2008, vol. 36, pp. 1046-1055.

* cited by examiner

*Primary Examiner* — Celine X Qian
(74) *Attorney, Agent, or Firm* — Thomas | Horstemeyer LLP

(57) ABSTRACT

Provided herein are genetically engineered cells containing one or more modulated metabolic genes, where the expression of the modulated metabolic gene(s) can be greater than that of an unmodified control. Also provided herein are methods of making the genetically engineered cells using synergistic activation mediator CRISPR-Cas9. Further provided herein are high throughput assays that can employ the genetically engineered cells provided herein.

2 Claims, 10 Drawing Sheets
Specification includes a Sequence Listing.

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: sgRNA CYP1A1

<400> SEQUENCE: 1
ctctctggga ttggagagaa                                            20

<210> SEQ ID NO 2
<211> LENGTH: 20
<212> TYPE: DNA
<213> ORGANISM: Artificial Sequence
<220> FEATURE:
<223> OTHER INFORMATION: sgRNA CYP1A1

<400> SEQUENCE: 2
gggtgggcaa gaacccacta                                            20

<210> SEQ ID NO 3
<211> LENGTH: 20
<212> TYPE: DNA
<213> ORGANISM: Artificial Sequence
<220> FEATURE:
<223> OTHER INFORMATION: sgRNA CYP1A1

```
<400> SEQUENCE: 3
agaagcagcc tgaaccgggc                                                    20

<210> SEQ ID NO 4
<211> LENGTH: 20
<212> TYPE: DNA
<213> ORGANISM: Artificial Sequence
<220> FEATURE:
<223> OTHER INFORMATION: sgRNA CYP3A4

<400> SEQUENCE: 4
actcaaagga ggtcagtgag                                                    20

<210> SEQ ID NO 5
<211> LENGTH: 20
<212> TYPE: DNA
<213> ORGANISM: Artificial Sequence
<220> FEATURE:
<223> OTHER INFORMATION: sgRNA CYP3A4

<400> SEQUENCE: 5
tggaagaggc ttctccacct                                                    20

<210> SEQ ID NO 6
<211> LENGTH: 20
<212> TYPE: DNA
<213> ORGANISM: Artificial Sequence
<220> FEATURE:
<223> OTHER INFORMATION: sgRNA CYP3A4

<400> SEQUENCE: 6
tgattctttg ccaacttcca                                                    20

<210> SEQ ID NO 7
<211> LENGTH: 20
<212> TYPE: DNA
<213> ORGANISM: Artificial Sequence
<220> FEATURE:
<223> OTHER INFORMATION: sgRNA CYP1A2

<400> SEQUENCE: 7
ggataggcca gaagggtgc                                                     20

<210> SEQ ID NO 8
<211> LENGTH: 20
<212> TYPE: DNA
<213> ORGANISM: Artificial Sequence
<220> FEATURE:
<223> OTHER INFORMATION: sgRNA CYP1A2

<400> SEQUENCE: 8
taagacccag ggtgactctt                                                    20

<210> SEQ ID NO 9
<211> LENGTH: 20
<212> TYPE: DNA
<213> ORGANISM: Artificial Sequence
<220> FEATURE:
<223> OTHER INFORMATION: sgRNA CYP1A2

<400> SEQUENCE: 9
gaaggatcaa ctcttggcct                                                    20

<210> SEQ ID NO 10
```

```
<211> LENGTH: 20
<212> TYPE: DNA
<213> ORGANISM: Artificial Sequence
<220> FEATURE:
<223> OTHER INFORMATION: sgRNA CYP2B6

<400> SEQUENCE: 10
gggataggca tcaggtcact                                                    20

<210> SEQ ID NO 11
<211> LENGTH: 20
<212> TYPE: DNA
<213> ORGANISM: Artificial Sequence
<220> FEATURE:
<223> OTHER INFORMATION: sgRNA CYP2B6

<400> SEQUENCE: 11
atgaaaaagg aggtggggaa                                                    20

<210> SEQ ID NO 12
<211> LENGTH: 20
<212> TYPE: DNA
<213> ORGANISM: Artificial Sequence
<220> FEATURE:
<223> OTHER INFORMATION: sgRNA CYP2B6

<400> SEQUENCE: 12
gggaacccag acttcctgct                                                    20

<210> SEQ ID NO 13
<211> LENGTH: 20
<212> TYPE: DNA
<213> ORGANISM: Artificial Sequence
<220> FEATURE:
<223> OTHER INFORMATION: sgRNA CYP2E1

<400> SEQUENCE: 13
ggaatcagcc tttgaaacga                                                    20

<210> SEQ ID NO 14
<211> LENGTH: 20
<212> TYPE: DNA
<213> ORGANISM: Artificial Sequence
<220> FEATURE:
<223> OTHER INFORMATION: sgRNA CYP2E1

<400> SEQUENCE: 14
ggtttattat tagctgctgt                                                    20

<210> SEQ ID NO 15
<211> LENGTH: 20
<212> TYPE: DNA
<213> ORGANISM: Artificial Sequence
<220> FEATURE:
<223> OTHER INFORMATION: sgRNA CYP2E1

<400> SEQUENCE: 15
agccagtgac ctggtgagga                                                    20

<210> SEQ ID NO 16
<211> LENGTH: 20
<212> TYPE: DNA
<213> ORGANISM: Artificial Sequence
<220> FEATURE:
<223> OTHER INFORMATION: sgRNA UGT1A6

<400> SEQUENCE: 16
```
ttctacacag gtcttgctct                                              20

<210> SEQ ID NO 17
<211> LENGTH: 20
<212> TYPE: DNA
<213> ORGANISM: Artificial Sequence
<220> FEATURE:
<223> OTHER INFORMATION: sgRNA UGT1A6

<400> SEQUENCE: 17
aagtctgttc tagtaattca                                              20

<210> SEQ ID NO 18
<211> LENGTH: 20
<212> TYPE: DNA
<213> ORGANISM: Artificial Sequence
<220> FEATURE:
<223> OTHER INFORMATION: sgRNA UGT1A6

<400> SEQUENCE: 18
cagagctagt catgcacacc                                              20

<210> SEQ ID NO 19
<211> LENGTH: 20
<212> TYPE: DNA
<213> ORGANISM: Artificial Sequence
<220> FEATURE:
<223> OTHER INFORMATION: sgRNA CYP2B6

<400> SEQUENCE: 19
tataacaggg tgcagaggca                                              20

<210> SEQ ID NO 20
<211> LENGTH: 20
<212> TYPE: DNA
<213> ORGANISM: Artificial Sequence
<220> FEATURE:
<223> OTHER INFORMATION: sgRNA CYP2B6

<400> SEQUENCE: 20
gtcaggataa aaggcccagt                                              20

<210> SEQ ID NO 21
<211> LENGTH: 20
<212> TYPE: DNA
<213> ORGANISM: Artificial Sequence
<220> FEATURE:
<223> OTHER INFORMATION: sgRNA CYP2B6

<400> SEQUENCE: 21
ggaggctgca gcagggtgca                                              20

<210> SEQ ID NO 22
<211> LENGTH: 20
<212> TYPE: DNA
<213> ORGANISM: Artificial Sequence
<220> FEATURE:
<223> OTHER INFORMATION: sgRNA CYP2E1

<400> SEQUENCE: 22
gcaagagggc attggttggt                                              20

<210> SEQ ID NO 23
<211> LENGTH: 20
<212> TYPE: DNA

```
<213> ORGANISM: Artificial Sequence
<220> FEATURE:
<223> OTHER INFORMATION: sgRNA CYP2E1

<400> SEQUENCE: 23
actcgtctat cccaaattac                                               20

<210> SEQ ID NO 24
<211> LENGTH: 20
<212> TYPE: DNA
<213> ORGANISM: Artificial Sequence
<220> FEATURE:
<223> OTHER INFORMATION: sgRNA CYP2E1

<400> SEQUENCE: 24
taaaaacctt ccgtttccac                                               20

<210> SEQ ID NO 25
<211> LENGTH: 20
<212> TYPE: DNA
<213> ORGANISM: Artificial Sequence
<220> FEATURE:
<223> OTHER INFORMATION: sgRNA UGT1A6

<400> SEQUENCE: 25
taggctgtcc cagtgagagg                                               20

<210> SEQ ID NO 26
<211> LENGTH: 20
<212> TYPE: DNA
<213> ORGANISM: Artificial Sequence
<220> FEATURE:
<223> OTHER INFORMATION: sgRNA UGT1A6

<400> SEQUENCE: 26
agctcaggtg aaagctgaca                                               20

<210> SEQ ID NO 27
<211> LENGTH: 20
<212> TYPE: DNA
<213> ORGANISM: Artificial Sequence
<220> FEATURE:
<223> OTHER INFORMATION: sgRNA UGT1A6

<400> SEQUENCE: 27
aattggcagg gggtcctcag                                               20

<210> SEQ ID NO 28
<211> LENGTH: 20
<212> TYPE: DNA
<213> ORGANISM: Artificial Sequence
<220> FEATURE:
<223> OTHER INFORMATION: sgRNA UGT1A9

<400> SEQUENCE: 28
agctcctatg atacagtagg                                               20

<210> SEQ ID NO 29
<211> LENGTH: 20
<212> TYPE: DNA
<213> ORGANISM: Artificial Sequence
<220> FEATURE:
<223> OTHER INFORMATION: sgRNA UGT1A9

<400> SEQUENCE: 29
ttccagacaa cagtagctta                                               20
```

```
<210> SEQ ID NO 30
<211> LENGTH: 20
<212> TYPE: DNA
<213> ORGANISM: Artificial Sequence
<220> FEATURE:
<223> OTHER INFORMATION: sgRNA UGT1A9

<400> SEQUENCE: 30
attggggtca ggttttgtgc                                                  20
```

METABOLICALLY COMPETENT CELLS, METHODS OF MAKING, AND USES THEREOF

CROSS-REFERENCE TO RELATED APPLICATIONS

This application is the 35 U.S.C. § 371 national stage application of PCT Application No. PCT/US17/41202, filed Jul. 7, 2017, where the PCT claims priority to, and the benefit of, U.S. provisional application entitled "METABOLICALLY COMPETENT CELLS, METHODS OF MAKING, AND USES THEREOF" having Ser. No. 62/359,479, filed Jul. 7, 2016, both of which are herein incorporated by reference in their entireties.

STATEMENT REGARDING FEDERALLY SPONSORED RESEARCH OR DEVELOPMENT

This invention was created using funds received from Grant Number Project #2017-10, awarded by the Johns Hopkins Bloomberg School of Public Health, Center for Alternatives to Animal Testing.

SEQUENCE LISTING

This application contains a sequence listing filed in electronic form as an ASCII.txt file entitled 222109-2730.txt, created on Jul. 7, 2017. The content of the sequence listing is incorporated herein in its entirety.

BACKGROUND

Out of thousands of chemicals in use today and in present our environment, very few have been fully evaluated for potential health risks. However, current in vitro tests are limited in their ability to provide useful results with respect to toxicity of a chemical or other agents due in part to differences in the cell lines used for the in vitro assays and the cells within the tissues of an organism. As such, there is an immediate need for improved in vitro toxicity assays to address the urgent public and environmental health need to identify the toxic effects of thousands of industrial, pharmaceutical, and environmental chemicals and other agents.

SUMMARY

Described in some aspects herein are genetically engineered cells that can contain one or more modulated metabolic genes, wherein the expression of the one or more modulated metabolic genes can be greater than the expression in an unmodified control cell. The genetically engineered cells can be an immortalized cell. The one or more modulated genes can be a cytochrome P450, phase I, or phase II gene. The genetically engineered cell can be metabolically competent. The genetically engineered cell can include in some aspects one or more sgRNAs for one or more metabolic genes. In some aspects, the genetically engineered cell can include a Cas9. In some aspects, the Cas9 can be inactive. In some aspects, the Cas9 can be operatively linked to a VP64 transcriptional activator. In some aspects, the genetically engineered cell can include one or more Cas9 transcriptional activators. The one or more Cas9 transcriptional activators can be a VP64 transcriptional activator, a MS2-p65-HSF1 co-activation complex, a MS2 RNA aptamer sgRNA, and combinations thereof. The one or more Cas9 transcriptional activators can form a synergistic activation mediator. In some aspects, the one or more modulated metabolic genes can be selected from the group set forth in Table 1 or any combination thereof.

Also described herein in some aspects are methods of producing a genetically engineered cell as described herein, where the method can include the step of enhancing transcription of one or more metabolic genes in a cell using synergistic activation mediator CRISPR-Cas9, wherein transcription of one or more metabolic genes can be increased as compared to an unmodified control cell.

Also described herein in some aspects are assays that can include the steps of exposing a genetically engineered cell as described herein with a test chemical or compound for a period of time and measuring a physiologic characteristic of the genetically engineered cell. The assay can further include the step of determining the toxicity of the test chemical or compound from the measured physiologic characteristic.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
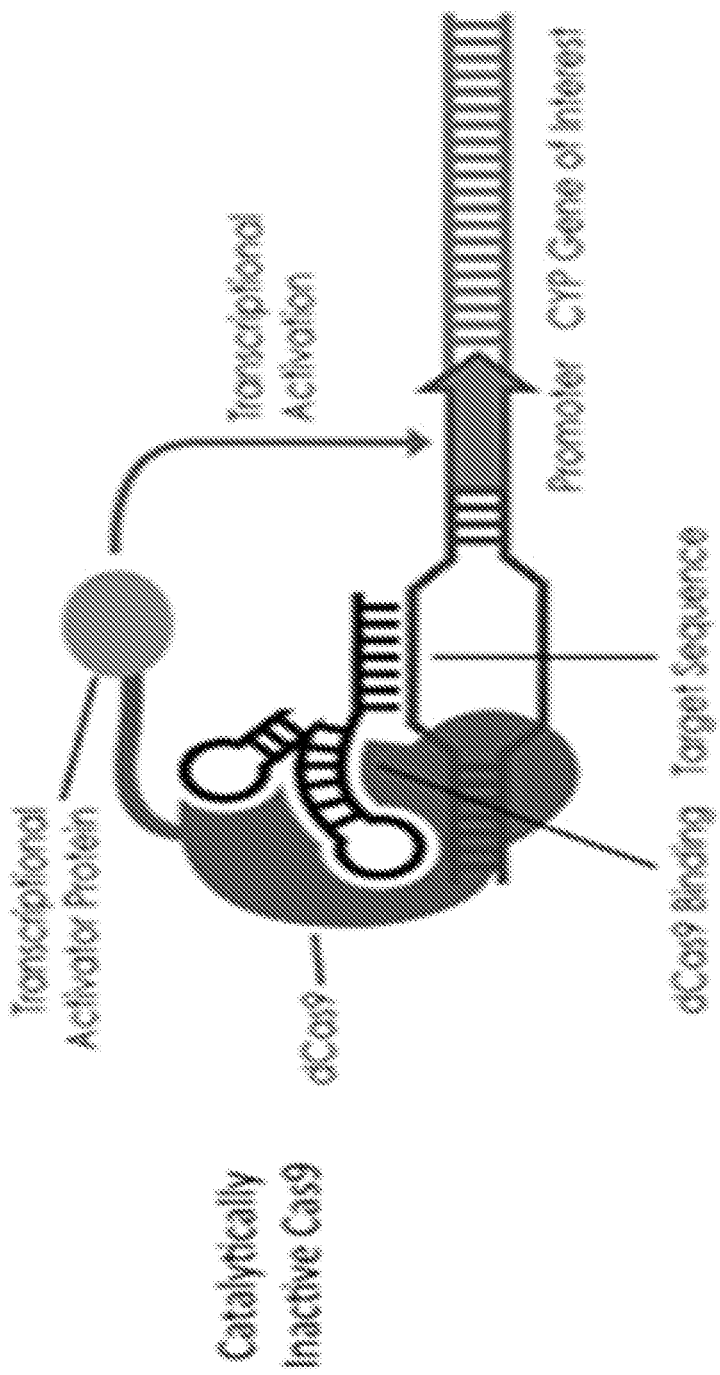
FIG. 1 shows a diagram of Cas9 based transcription activation.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, toxicology, pharmacology, physiology, organic chemistry, biochemistry, botany and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "deoxyribonucleic acid (DNA)" and "ribonucleic acid (RNA)" can refer to any polyribonucleotide or polydeoxyribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA. Similarly "RNA molecule" includes nucleic acids/polynucleotides that are made of RNA.

As used herein, "gene" refers to a hereditary unit corresponding to a sequence of DNA that occupies a specific location on a chromosome and that contains the genetic instruction for a characteristic(s) or trait(s) in an organism. The term "gene" encompasses specific nucleotide sequences of a genome that are transcribed into an RNA product and are not translated into a protein as well as those genomic sequences that are transcribed into an RNA product yet are translated into a protein.

As used herein, "locus" refers to the position that a given gene or portion thereof occupies on a chromosome of a given species.

As used herein, the term "exogenous DNA" or "exogenous nucleic acid sequence" or "exogenous polynucleotide" refers to a nucleic acid sequence that was introduced into a cell, organism, or organelle via transfection. Exogenous nucleic acids originate from an external source, for instance, the exogenous nucleic acid may be from another cell or organism and/or it may be synthetic and/or recombinant. While an exogenous nucleic acid sometimes originates from a different organism or species, it may also originate from the same species (e.g., an extra copy or recombinant form of a nucleic acid that is introduced into a cell or organism in addition to or as a replacement for the naturally occurring nucleic acid). Typically, the introduced exogenous sequence is a recombinant sequence.

As used herein, the term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a "fusion protein" (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g, a nucleic acid and a constitutive promoter), etc.). Recombinant also refers to the polypeptide encoded by the recombinant nucleic acid. Non-naturally occurring nucleic acids or polypeptides include nucleic acids and polypeptides modified by man.

As used herein, "polypeptides" or "proteins" are as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein "peptide" refers to chains of at least 2 amino acids that are short, relative to a protein or polypeptide.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

As used herein, "functional variant" refers to a variant of a protein or polypeptide (e.g., a variant of a Cas9 protein) that can perform the same functions or activities as the original protein or polypeptide, although not necessarily at the same level (e.g., the variant may have enhanced, reduced or changed functionality, so long as it retains the basic function).

As used herein, "identity," is a relationship between two or more polypeptide or nucleic acid sequences, as determined by comparing the sequences. In the art, "identity" also refers to the degree of sequence relatedness between polypeptides or nucleic acid sequences as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure.

As used herein, "plasmid" as used herein refers to a non-chromosomal double-stranded DNA sequence including an intact "replicon" such that the plasmid is replicated in a host cell.

As used herein, the term "vector" or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, "promoter" includes all sequences capable of driving transcription of a gene. In particular, the term "promoter" as used herein can refer to a DNA sequence generally described as the 5' regulator region of a gene, located proximal to the start codon. The transcription of an adjacent gene sequence is initiated at the promoter region. The term "promoter" also includes fragments of a promoter that are functional in initiating transcription of the gene. The term "promoter" can encompass constitutive promoters and inducible promoters.

As used herein, "constitutive promoter" is a promoter that allows for continual or ubiquitous transcription of its associated gene or polynucleotide. Constitutive promoters are generally are unregulated by cell or tissue type, time, or environment.

As used herein, "inducible promoter" is a promoter that allows transcription of its associated gene or polynucleotide in response to a substance or compound (e.g. an antibiotic, or metal), an environmental condition (e.g. temperature), developmental stage, or tissue type.

As used herein, "wild-type" is the average form of an organism, variety, strain, gene, protein, or characteristic as it occurs in a given population in nature, as distinguished from mutant forms that may result from selective breeding, recombinant engineering, and/or transformation with a transgene.

As used herein, "operatively linked" indicates that the regulatory sequences useful for expression of the coding sequences of a nucleic acid are placed in the nucleic acid molecule in the appropriate positions relative to the coding sequence so as to effect expression of the coding sequence. This same definition is sometimes applied to the arrangement of coding sequences and transcription control elements (e.g. promoters, enhancers, and termination elements), and/or selectable markers in an expression vector.

As used herein, "expression" as used herein describes the process undergone by a structural gene to produce an RNA molecule and/or polypeptide. It can refer to the combination of transcription and translation. Expression can refer to the "expression" of a nucleic acid to produce a RNA molecule and can also refers to "expression" of a polypeptide, indicating that the polypeptide is being produced via expression of the corresponding nucleic acid.

As used herein, "selectable marker" refers to a gene whose expression allows one to identify cells that have been transformed or transfected with a vector containing the marker gene. For instance, a recombinant nucleic acid may include a selectable marker operatively linked to a gene of interest and a promoter, such that expression of the selectable marker indicates the successful transformation of the cell with the gene of interest.

The terms "guide polynucleotide," "guide sequence," or "guide RNA" can refer to any polynucleotide sequence having sufficient complementarity with a target polynucleotide sequence to hybridize with the target sequence and direct sequence-specific binding of a CRISPR complex to the target sequence. The degree of complementarity between a guide polynucleotide and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). A guide polynucleotide (also referred to herein as a guide sequence and includes single guide sequences (sgRNA)) can be about or more than about 5, 10, 11, 12, 13, 14, 15, 16, 17, 18, 19, 20, 21, 22, 23, 24, 25, 26, 27, 28, 29, 30, 35, 40, 45, 50, 75, 90, 100, 110, 112, 115, 120, 130, 140, or more nucleotides in length. The guide polynucleotide can include a nucleotide sequence that is complementary to a target DNA sequence. This portion of the guide sequence can be referred to as the complementary region of the guide RNA. In some contexts, the two are distinguished from one another by calling one the complementary region or target region and the rest of the polynucleotide the guide sequence or tracrRNA. The guide sequence can also include one or more miRNA target sequences coupled to the 3' end of the guide sequence. The guide sequence can include one or more MS2 RNA aptamers incorporated within the portion of the guide strand that is not the complementary portion. As used herein the term guide sequence can include any specially modified guide sequences, including but not limited to those configured for use in synergistic activation mediator (SAM) implemented CRISPR (*Nature* 517, 583-588 (29 Jan. 2015). A guide polynucleotide can be less than about 150, 125, 75, 50, 45, 40, 35, 30, 25, 20, 15, 12, or fewer nucleotides in length. The ability of a guide polynucleotide to direct sequence-specific binding of a CRISPR complex to a target sequence may be assessed by any suitable assay. For example, the components of a CRISPR system sufficient to form a CRISPR complex, including the guide polynucleotide to be tested, may be provided to a host cell having the corresponding target sequence, such as by transfection with vectors encoding the components of the CRISPR sequence, followed by an assessment of preferential cleavage within the target sequence. Similarly, cleavage of a target polynucleotide sequence may be evaluated in a test tube by providing the target sequence, components of a CRISPR complex, including the guide polynucleotide to be tested and a control guide polynucleotide different from the test guide polynucleotide, and comparing binding or rate of cleavage at the target sequence between the test and control guide polynucleotide reactions. Other assays are possible, and will occur to those skilled in the art.

A complementary region of the gRNA can be configured to target any DNA region of interest. The complementary region of the gRNA and the gRNA can be designed using a suitable gRNA design tool. Suitable tools are known in the art and are available to the skilled artisan. Some such tools are discussed elsewhere herein. As such, the constructs described herein are enabled for any desired target DNA so long as it is CRISPR compatible according to the known requirements for CRISPR activation. A guide polynucleotide can be selected to reduce the degree of secondary structure within the guide polynucleotide. Secondary structure may be determined by any suitable polynucleotide folding algorithm. Some programs are based on calculating the minimal Gibbs free energy. An example of one such algorithm is mFold, as described by Zuker & Stiegler ((1981) *Nucleic Acids Res.* 9, 133-148). Another example folding algorithm is the online webserver RNAfold, developed at Institute for Theoretical Chemistry at the University of Vienna, using the centroid structure prediction algorithm (see e.g. Gruber et al., (2008) *Cell* 106: 23-24; and Carr & Church (2009) *Nature Biotechnol.* 27: 1151-1162).

Homology-directed repair (HDR) refers to a mechanism in cells to repair double-stranded and single stranded DNA breaks. Homology-directed repair includes homologous recombination (HR) and single-strand annealing (SSA) (Lieber. (2010) *Annu. Rev. Biochem.* 79: 181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks.

Error-prone DNA repair refers to mechanisms that can produce mutations at double-strand break sites. The Non-Homologous-End-Joining (NHEJ) pathways are the most common repair mechanism to bring the broken ends together (Bleuyard et al., (2006) *DNA Repair* 5: 1-12). The structural integrity of chromosomes is typically preserved by the repair, but deletions, insertions, or other rearrangements are possible. The two ends of one double-strand break are the most prevalent substrates of NHEJ (Kirk et al., (2000) *EMBO J.* 19: 5562-5566), however if two different double-strand breaks occur, the free ends from different breaks can be ligated and result in chromosomal deletions (Siebert & Puchta, (2002) *Plant Cell* 14:1121-1131), or chromosomal translocations between different chromosomes (Pacher et al., (2007) Genetics 175: 21-29).

It will also be appreciated that CRISPR can also be used to activate specific genes through CRISPR/synergistic activation mediator procedures. These procedures can utilize a guide polynucleotide that incorporates 2 MS2 RNA aptamers at the tetraloop and the stem-loop of the guide RNA such as that described in, but not limited to (*Nature* 517, 583-588 (29 Jan. 2015).

As used herein, "specific binding" refers to binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

The terms "Cas9" and "Cas9 polypeptide" are used interchangeably herein to refer to an enzyme (wild-type or recombinant) that can exhibit least endonuclease activity (e.g. cleaving the phosphodiester bond within a polynucleotide) guided by a CRISPR RNA (crRNA) bearing complementary sequence to a target polynucleotide. Cas9 polypeptides are known in the art, and include Cas9 polypeptides from any of a variety of biological sources, including, e.g., prokaryotic sources such as bacteria and archaea. Bacterial Cas9 includes, Actinobacteria (e.g., *Actinomyces naeslundii*) Cas9, Aquificae Cas9, Bacteroidetes Cas 9, Chlamydiae Cas9, Chloroflexi Cas9, Cyanobacteria Cas9, Elusimicrobia Cas9, Fibrobacteres Cas9, Firmicutes Cas9 (e.g., *Streptococcus pyogenes* Cas9, *Streptococcus thermophilus* Cas9, *Listeria innocua* Cas9, *Streptococcus agalactiae* Cas9, *Streptococcus mutans* Cas9, and *Enterococcus faecium* Cas9), Fusobacteria Cas9, Proteobacteria (e.g., *Neisseria meningitides, Campylobacter jejuni* and *lari*) Cas9, Spirochaetes (e.g., *Treponema denticola*) Cas9, and the like. Archaea Cas 9 includes Euryarchaeota Cas9 (e.g., *Methanococcus maripaludis* Cas9) and the like. A variety of Cas9 and related polypeptides are known, and are reviewed in, e.g., Makarova et al. (2011) Nature Reviews Microbiology 9:467-477, Makarova et al. (2011) Biology Direct 6:38, Haft et al. (2005) PLOS Computational Biology I:e60 and Chylinski et al. (2013) RNA Biology 10:726-737. Other Cas9 polypeptides can be *Francisella tularensis* subsp. *novicida* Cas9, *Pasteurella multocida* Cas9, *Mycoplasma gallisepticum* str. F Cas9, *Nitratifractor salsuginis* str DSM 16511 Cas9, *Parvibaculum lavamentivorans* Cas9, *Roseburia intestinalis* Cas9, *Neisseria cinera* Cas9, *Gluconacetobacter diazotrophicus* Cas9, Azospirillum B510 Cas9, *Spaerochaeta globus* str. Buddy cas9, *Flavobacterium columnare* Cas9, *Fluviicola taffensis* Cas9, *Bacteroides coprophilus* Cas9, *Mycoplasma mobile* Cas9, *Lactobacillus farciminis* Cas9, *Streptococcus pasteurianus* Cas9, *Lactobacillus johnsonii* Cas9, *Staphylococcus pseudintermedius* Cas9, *filifactor alocis* Cas9, *Treponema denticola* Cas9, *Legionella pneumophila* str. Paris Cas9, *Sutterella wadsworthensis* Cas9, and *Corynebacter diptheriae* Cas9. The term "Cas9" includes a Cas9 polypeptide of any Cas9 family, including any isoform of Cas9. Amino acid sequences of various Cas9 homologs, orthologs, and variants beyond those specifically stated or provided herein are known in the art and are publicly available, within the purview of those skill in the art, and thus within the spirit and scope of this disclosure.

As used herein, "inactive Cas9" refers to a Cas9 that lacks endonuclease activity.

As used herein with reference to the relationship between DNA, cDNA, cRNA, RNA, and protein/peptides, "corresponding to" refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein "metabolically competent" can refer to the manipulation, such as through genetic engineering, of the gene expression profile of a cell such that it expresses one or more metabolic related genes (including but not limited to those listed in Table 1 herein) at a different level (e.g. expressed at a greater lever or a reduced level) when compared to the unmodified cell.

As used herein "gene (or protein) expression profile" can refer to the gene (or protein) expression pattern observed across two or more genes in a cell, tissue, organ, and/or organism. In some instances, the gene (or protein) expression profile reflects the typical gene (or protein) for a type of cell, tissue, etc. across a population.

Discussion

There is an urgent public health need to identify the toxic effects of thousands of industrial, pharmaceutical, and environmental chemicals. High throughput screening (HTS) assays rely on cells to rapidly screen for the toxic effect of chemicals. In vitro HTS assays that utilize immortalized human cell lines could circumvent current animal models, which are time consuming, costly and present ethical concerns. However, immortalized cells have different metabolic profiles from in vivo or in situ cells, which are typically the cells for which toxicity information is desired. For example, immortalized cells typically have poor, if any, expression of genes involved in metabolism of chemicals, such as cytochrome P450 enzymes. These metabolic inaccuracies between immortalized cells and in vivo cells limit the accuracy of current in vitro toxicity tests and other in vitro assays using immortalized cell lines. As such, there exists a need for immortalized cell lines with an improved metabolic profile for HTS toxicity assays.

With that said, described herein are metabolically competent cells that can be suitable for use in HTS assays, including but not limited to HTS toxicity assays. In embodiments, the cells can be genetically engineered to express one or more cytochrome P450 enzyme genes. The metabolically competent cells described herein can be generated using a SAM-mediated CRISPR-Cas9 system (or other CRISPR-Cas9 based transcriptional activation approach) to induce expression of one or more cytochrome P450 genes. Also described herein are methods of screening chemicals and other compounds by exposing a metabolically competent cell or population thereof described herein with one or more chemicals or other compounds and measuring toxicity, metabolite production, and/or other relevant cellular endpoints of interest. The cells and methods provided herein can improve existing in vitro screening tests by allowing for intracellular metabolic transformations and providing toxicity data, or other cellular endpoints of interest that require metabolic transformation that is more accurate and more reflective of the in vivo situation, and for the assessment of the role of cytochrome P450 allelic variation in xenobiotic metabolism toxicity and other biological activity.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Metabolically Competent Cells

Described herein are genetically engineered cells that can be metabolically competent. The genetically engineered cells can include one or more modulated metabolic genes, where the expression of the modulated metabolic gene(s) is greater than the expression in an unmodified cell. The modulated metabolic gene(s) can be, without limitation, any of the genes listed in Table 1 and any combination thereof. In embodiments, the metabolic gene(s) can be a cytochrome P450 gene(s). Table 1 shows exemplary CYP450 and other phase I and II metabolic genes related to chemical toxicity.

TABLE 1

| Gene Symbol | Gene Name | Representative GenBank Accession Number |
| --- | --- | --- |
| ADH1A | alcohol dehydrogenase 1A | AY948115 |
| ADH4 | alcohol dehydrogenase 4 | AY974245 |
| ADH5 | alcohol dehydrogenase 5 | AH002555 |
| ADH6 | alcohol dehydrogenase 6 | AY962311 |
| ADH7 | alcohol dehydrogenase 7 | AH006682 |
| AKR1B1 | aldo-keto reductase family 1, member B1 (aldose reductase) | CR542203 |
| AKR1C1 | aldo-keto reductase family 1, member C1 | AB032150.1 |
| AKR1C2 | aldo-keto reductase family 1, member C2 | AB032153.2 |
| AKR1C3 | aldo-keto reductase family 1, member C3 | AB028065.1 |
| AKR7A2 | aldo-keto reductase family 7, member A2 (aflatoxin aldehyde reductase) | AL035413.19 |
| ALDH18A1 | aldehyde dehydrogenase 18 family, member A1 | AL356632.12 |
| ALDH1A1 | aldehyde dehydrogenase 1 family, member A1 | AL591031.3 |
| ALDH1A2 | aldehyde dehydrogenase 1 family, member A2 | AC012653.8 |
| ALDH1A3 | aldehyde dehydrogenase 1 family, member A3 | AC015712.10 |
| ALDH2 | aldehyde dehydrogenase 2 family (mitochondrial) | AC002996.1 |
| ALDH3A1 | aldehyde dehydrogenase 3 family, memberA1 | AC005722.1 |
| ALDH3A2 | aldehyde dehydrogenase 3 family, member A2 | AC005722.1 |
| ALDH3B1 | aldehyde dehydrogenase 3 family, member B1 | 1 |
| ALDH3B2 | aldehyde dehydrogenase 3 family, member B2 | |
| ALDH4A1 | aldehyde dehydrogenase 4 family, member A1 | AL080251.23 |
| ALDH5A1 | aldehyde dehydrogenase 5 family, member A1 | AL031230.1 |
| ALDH6A1 | aldehyde dehydrogenase 6 family, member A1 | AC005484.2 |
| ALDH7A1 | aldehyde dehydrogenase 7 family, member A1 | U10868 |
| ALDH8A1 | aldehyde dehydrogenase 8 family, member A1 | AF303134 |
| ALDH9A1 | aldehyde dehydrogenase 9 family, member A1 | AL451074 |
| CES1 | carboxylesterase 1 (monocyte/macrophage serine esterase 1) | AB119997.1 |
| CES2 | carboxylesterase 2 (intestine, liver) | AC009084 |
| CES3 | carboxylesterase 3 | EU595874 |
| COMT | catechol-O-methyltransferase | AC000080 |
| CYP11A1 | cytochrome P450, family 11, subfamily A, polypeptide 1 | NG_007973.1 |
| CYP11B1 | cytochrome P450, family 11, subfamily B, polypeptide 1 | AC083841 |
| CYP11B2 | cytochrome P450, family 11, subfamily B, polypeptide 2 | AC073385 |
| CYP17A1 | cytochrome P450, family 17, subfamily A, polypeptide 1 | AH002665.2 |
| CYP19A1 | cytochrome P450, family 19, subfamily A, polypeptide 1 | AC012169 |
| CYP1A1 | cytochrome P450, family 1, subfamily A, polypeptide 1 | NG_008431.2 |

TABLE 1-continued

| Gene Symbol | Gene Name | Representative GenBank Accession Number |
|---|---|---|
| CYP1A2 | cytochrome P450, family 1, subfamily A, polypeptide 2 | NG_008431 |
| CYP1B1 | cytochrome P450, family 1, subfamily B, polypeptide 1 | AH011662.2 |
| CYP21A2 | cytochrome P450, family 21, subfamily A, polypeptide 2 | NT_167249.2 |
| CYP24A1 | cytochrome P450, family 24, subfamily A, polypeptide 1 | AL138805.8 |
| CYP26A1 | cytochrome P450, family 26, subfamily A, polypeptide 1 | NC_000010.11 |
| CYP26B1 | cytochrome P450, family 26, subfamily B, polypeptide 1 | NC_000002.12 |
| CYP26C1 | cytochrome P450, family 26, subfamily C, polypeptide 1 | AL358613.16 |
| CYP27A1 | cytochrome P450, family 27, subfamily A, polypeptide 1 | NC_000002.12 |
| CYP27B1 | cytochrome P450, family 27, subfamily B, polypeptide 1 | AB006987.1 |
| CYP2A13 | cytochrome P450, family 2, subfamily A, polypeptide 13 | NC_000019.10 |
| CYP2A6 | cytochrome P450, family 2, subfamily A, polypeptide 6 | NG_008377.1 |
| CYP2B6 | cytochrome P450, family 2, subfamily B, polypeptide 6 | AC011541.7 |
| CYP2C18 | cytochrome P450, family 2, subfamily C, polypeptide 18 | AH000016.2 |
| CYP2C19 | cytochrome P450, family 2, subfamily C, polypeptide 19 | AF354181.1 |
| CYP2C8 | cytochrome P450, family 2, subfamily C, polypeptide 8 | AF136833.1 |
| CYP2C9 | cytochrome P450, family 2, subfamily C, polypeptide 9 | AH007329.2 |
| CYP2D6 | cytochrome P450, family 2, subfamily D, polypeptide 6 | NG_008376, REGION: 4111 . . . 8493 |
| CYP2E1 | cytochrome P450, family 2, subfamily E, polypeptide 1 | NG_008383.1 |
| CYP2F1 | cytochrome P450, family 2, subfamily F, polypeptide 1 | AH011393.2 |
| CYP2J2 | cytochrome P450, family 2, subfamily J, polypeptide 2 | Y426985.1 |
| CYP2R1 | cytochrome P450, family 2, subfamily R, polypeptide 1 | BC104907.1 |
| CYP2S1 | cytochrome P450, family 2, subfamily S, polypeptide 1 | AF335278.1 |
| CYP2W1 | cytochrome P450, family 2, subfamily W, polypeptide 1 | BC025761.1 |
| CYP3A4 | cytochrome P450, family 3, subfamily A, polypeptide 4 | AF182273.1 |
| CYP3A43 | cytochrome P450, family 3, subfamily A, polypeptide 43 | AF280108.1 |
| CYP3A5 | cytochrome P450, family 3, subfamily A, polypeptide 5 | AF355800.1, AF355803.1 |
| CYP46A1 | cytochrome P450, family 46, subfamily A, polypeptide 1 | AL136000 |
| CYP4A11 | cytochrome P450, family 4, subfamily A, polypeptide 11 | AF525488 |
| CYP4A22 | cytochrome P450, family 4, subfamily A, polypeptide 22 | AF208532 |
| CYP4B1 | cytochrome P450, family 4, subfamily B, polypeptide 1 | AF491285 |
| CYP4F11 | cytochrome P450, family 4, subfamily F, polypeptide 11 | AF236085 |
| CYP4F12 | similar to cytochrome P450, family 4, subfamily F, polypeptide 12 | AB035130.1 |
| CYP4F2 | cytochrome P450, family 4, subfamily F, polypeptide 2 | AB015306.2 |
| CYP4F3 | cytochrome P450, family 4, subfamily F, polypeptide 3 | AB002461.2 |
| CYP4F8 | cytochrome P450, family 4, subfamily F, polypeptide 8 | AF133298.1 |
| CYP4V2 | cytochrome P450, family 4, subfamily V, polypeptide 2 | FJ440682.1 |
| CYP51A1 | cytochrome P450, family 51, subfamily A, polypeptide 1 | AH006655.4 |
| CYP7A1 | cytochrome P450, family 7, subfamily A, polypeptide 1 | BC101777.1 |
| CYP7B1 | cytochrome P450, family 7, subfamily B, polypeptide 1 | AH010394.2 |
| CYP8B1 | cytochrome P450, family 8, subfamily B, polypeptide 1 | AF090320.1 |
| EPHX1 | epoxide hydrolase 1, microsomal (xenobiotic) | AF253417 L25880 L29766 |
| EPHX2 | epoxide hydrolase 2, cytoplasmic | AF233334.1 |
| FMO1 | flavin containing monooxygenase 1 | AY879266.1 |
| FMO2 | flavin containing monooxygenase 2 (non-functional) | AY916056.1 |
| FMO3 | flavin containing monooxygenase 3 | AY895830.1 |
| FMO4 | flavin containing monooxygenase 4 | AY882422.1 |
| FMO5 | flavin containing monooxygenase 5 | AY902236.1 |
| GSTA1 | glutathione S-transferase alpha 1 | AH003831.2 |
| GSTA3 | glutathione S-transferase alpha 3 | AH003187.2 |
| GSTA4 | glutathione S-transferase alpha 4 | AH006981.2 |
| GSTA5 | glutathione S-transferase alpha 5 | BK000212.1 |
| HNMT | histamine N-methyltransferase | AH003685.2 |
| MAOA | monoamine oxidase A | AH002871.2 |
| MAOB | monoamine oxidase B | AH002872.2 |
| NAT1 | N-acetyltransferase 1 (arylamine N-acetyltransferase) | AF008204.1 |
| NAT2 | N-acetyltransferase 2 (arylamine N-acetyltransferase) | AY331807.1 |
| NNMT | nicotinamide N-methyltransferase | EF445002.1 |
| POR | P450 (cytochrome) oxidoreductase | DQ640499.1 |
| SULT1A1 | sulfotransferase family, cytosolic, 1A, phenol-preferring, member 1 | U52852.2 |
| SULT1A2 | sulfotransferase family, cytosolic, 1A, phenol-preferring, member 2 | U33886.1 |
| SULT1A3 | sulfotransferase family, cytosolic, 1A, phenol-preferring, member 3 | U20499.1 |
| SULT1B1 | sulfotransferase family, cytosolic, 1B, member 1 | BC010895.1 |
| SULT1C2 | sulfotransferase family, cytosolic, 1C, member 2 | H009383.2 |
| SULT1C3 | sulfotransferase family, cytosolic, 1C, member 3 | |
| SULT1C4 | sulfotransferase family, cytosolic, 1C, member 4 | BC058861.1 |
| SULT1E1 | sulfotransferase family 1E, estrogen-preferring, member 1 | AY436634.1 |
| SULT2A1 | sulfotransferase family, cytosolic, 2A, dehydroepiandrosterone (DHEA)-preferring, member1 | AH003200.2 |
| SULT2B1 | sulfotransferase family, cytosolic, 2B, member 1 | AH007006.2 |
| SULT4A1 | sulfotransferase family 4A, member 1 | AF115311.1 |
| SULT6B1 | sulfotransferase family, cytosolic, 6B, member 1 | BK001437.1 |
| TPMT | thiopurine S-methyltransferase | AB045146.1 |
| UGT1A1 | UDP glucuronosyltransferase 1 family, polypeptide A1 | LC005519.1 |
| UGT2A1 | UDP glucuronosyltransferase 2 family, polypeptide A1 | AJ006054.1 |
| UGT2A3 | UDP glucuronosyltransferase 2 family, polypeptide A3 | BC130533.1 |
| UGT2B10 | UDP glucuronosyltransferase 2 family, polypeptide B10 | BC113649.1 |
| UGT2B17 | UDP glucuronosyltransferase 2 family, polypeptide B17 | U59209.1 |
| UGT2B28 | UDP glucuronosyltransferase 2 family, polypeptide B28 | AF177272.1 |
| UGT2B4 | UDP glucuronosyltransferase 2 family, polypeptide B4 | DQ520733.1 |
| UGT2B7 | UDP glucuronosyltransferase 2 family, polypeptide B7 | BC030974.1 |
| UGT3A1 | UDP glycosyltransferase 3 family, polypeptide A1 | BC035012.1 |
| UGT8 | UDP glycosyltransferase 8 | AH006651.2 |

The genetically engineered cells can be any cell line, including but not limited to an immortalized cell line, that are generally known in the art, where the cell line has been genetically modified such that it expresses one or more metabolic genes at a level greater than an unmodified cell of the same cell line. Immortalized cell lines that can be genetically engineered as described herein include, but are not limited to, HEK293, HepG2, Huh7, HepaRG, K562, HeLa, BEAS-2B and A549. The genetically engineered cells can be derived from any tissue in an organism, including but not limited to, liver, heart, kidney, brain hematopoietic system, skin, spleen, lung, and intestine.

As discussed in greater detail below, the genetically engineered cells can be generated using a SAM CRISPR-Cas9 system or similar CRISPR-Cas9 activation system. The genetically engineered cells can contain one or more sgRNAs directed to one or more metabolic genes. The genetically engineered cells can contain Cas9. In some embodiments, the Cas9 can be an inactive Cas9. In some embodiments, the inactive Cas9 can be a Cas9 that is operatively linked to a VP64 transcriptional activator. The genetically engineered cells can contain one or more Cas9 transcriptional activators. The transcriptional activator(s) can be, without limitation, VP64 transcriptional activator, a MS2-p65-HSF1 co-activation complex, a MS2 RNA aptamer sgRNA, and any combination thereof. In embodiments, the transcriptional activators can form a synergistic activation mediator (SAM). It will be appreciated that any of these CRISPR related components can be present in the genetically engineered cell transiently (i.e. not integrated into the genome of the cell) or stably (i.e. integrated into the genome of the genetically engineered cell or stable episomal integration (e.g. episomal amplification from an SV40 origin of replication in a plasmid)). In some embodiments, some components may be transiently present in the genetically engineered cell while others may be stably present in the genetically engineered cell.

Methods of Making Metabolically Competent Cells

Described herein are CRISPR-Cas9 based methods of generating the metabolically competent genetically engineered cells. The method can include the step of enhancing the transcription of one or more metabolic genes in a cell using synergistic activation mediator (SAM) CRISPR-Cas9, where transcription of the one or more metabolic genes is increased as compared to an unmodified control cell. The metabolically competent cells can be made by transiently expressing one or more of the SAM CRISPR-Cas9 components. In other embodiments, the metabolically competent cells can be made by stably incorporating and expressing one or more of the SAM CRISPR-Cas9 system, such as the invariant components.

Transient introduction of all (or some) of the components allows for components needed to modulate metabolic gene expression immediately prior to each high throughput screening (HTS) assay. This approach can be useful for cell lines that are not suitable for stable integration. Methods of transient introduction (e.g. transfection or viral transduction or infection) are generally known in the art. After transient introduction of the components, short or long-term induction can be conducted to allow for expression of the metabolic genes to produce cells that can be used in a HTS assay. Metabolic gene expression can be confirmed using reverse transcription polymerase chain reaction (RT-PCR), quantitative RT-PCR or other suitable method, which will be appreciated by one of ordinary skill in the art. Other assays can be used to measure gene transcription or other activity of the gene or gene product. These can be specific to the particular genes of interest. Standard assays for measuring particular gene activity will be instantly appreciated by those of skill in the art. For example, P450 activity can be measured using an EROD assays.

Stable introduction can be used to introduce some, such as the invariant SAM CRISPR-Cas9 components (e.g. not the sgRNA), or all of the components. In situations where it is desirable to stably incorporate the sgRNA, a DNA encoding the desired sgRNA can be stably incorporated into the cell. Cells with stable integration of the desired components can be selected for using methods generally known in the art. sgRNA can also be delivered transiently via a DNA vector that can express the sgRNA. In embodiments, where only the invariant SAM CRISPR-Cas9 components have been stably incorporated, prior the HTS assay, the sgRNA can be introduced transiently using any appropriate method. After transient introduction of the components, short or long-term induction can be conducted to allow for expression of the metabolic genes to produce cells that can be used in a HTS assay. Metabolic gene expression can be confirmed using reverse transcription polymerase chain reaction (RT-PCR), quantitative RT-PCR or other suitable method, which will be appreciated by one of ordinary skill in the art.

Multiple metabolic genes can be activated simultaneously through the simultaneous expression of multiple sgRNAs in a suitable expression vector. Such expression vectors will be appreciated by those of ordinary skill in the art. In other embodiments, multiple vectors each configured to express one or more sgRNAs can be transiently or stably introduced into a cell to achieve simultaneous activation of multiple metabolic genes. In further embodiments, multiple metabolic genes can be activated simultaneously by transient delivery of a pool of sgRNAs to the cell. The pools can contain any desired group of sgRNAs selected from any provided and/or described herein. As demonstrated in FIGS. 4-10, we have successfully used this method to activate CYP1A2, CYP2B6, CYP2E1, CYP3A4, and UGT1A6 in HEK293T cell lines, although the technique could be applied to any cell line receptive to transfection. Additionally, the strategy described herein could be potentially used to activate any other desired gene or suite of genes. sgRNAs can be designed based of the gene and/or coding sequence information available to one of ordinary skill in the art, including that from the major publically available databases, including but not limited to GenBank. Algorithms and design considerations for sgRNAs are described elsewhere herein and available through publically accessible resources, companies, and the body of peer-reviewed literature.

The approaches described herein can be scaled as desired. Transient or stable C-MAGIC can be scalable to as many multi-well plates as needed for the assay described elsewhere herein. For transient approaches, the lentivirus transduction and plasmid construction can be appropriately scaled to provide sufficient cell number. It is not expected that CRISPR based activation will have any toxicity. The expression of P450s in the cell line is not expected to interfere with any of the established endpoints.

The approaches described herein can be scalable and replicable. Using lentiviral transduction, stable cell lines in which a single or multiple metabolic enzymes are transcriptionally induced can be generated. A particular stable cell line can be grown and multiplied to obtain a large number of cells that is enough to perform large-scale experiments or to perform multiple replicates of each experimental condition (exposure). The stable cell line can be maintained in culture or cryopreserved in liquid nitrogen to be used whenever repeating an experiment is necessary. In addition, induction of multiple metabolic enzymes in a reporter cell line using transient transfection is also scalable and replicable. Transient transfection of cells can be scaled-up by proportionally increasing the number of cultured cells, transfection reagents and quantity of the plasmids used. Also, the current transfection reagents can provide efficient transfection that can be consistently replicated.

The constructs and methods provided herein are compatible with existing cell lines demonstrated for use in HTS. CRISPR based activation can be compatible with currently used cell based assays and cell lines. For either the proposed transient or stable approach, selection can be used to ensure a uniform population of cells expressing the sgRNA and CRISPR-Cas9 Fusion. CRISPR vectors can alternatively be selected or modified to use an alternative selectable marker. In addition, in a transient approach using Lentivirus, the infection efficiency is typically high and can be up to 100% so, in some embodiments, there may be no need for selection of transfected or transduced cells. The transient CRISPR based activation approach can include a period of time (about 1 hour) to induce the expression of the metabolic genes. Once induced, it is expected that there would be stable induction and protein production for at least 48 hrs based on the stability of other transient transfection vectors. The stable C-MAGIC approach would be constitutively expressing the metabolic gene(s) of interest so the expression should be at steady state throughout the experiment.

Methods of Using the Metabolically Competent Cells

The genetically engineered cells described herein can be used in a screening assay, such as a HTS assay, to determine the effect, such as toxicity, of one or more chemicals or other compounds on a cell. After generation, the cells can be seeded at an appropriate density in wells on a cell or tissue culture plate. In embodiments, a screening assay can include the step of exposing a genetically engineered cell as described herein with a test chemical or compound for a period of time and measuring a physiologic characteristic of the genetically engineered cell. A change in the physiologic characteristic due to the chemical or compound can be determined by comparing the measurement of the physiologic characteristic to one or more controls (e.g. negative controls and positive controls). In some embodiments, the physiologic characteristic is measured directly, such as by measuring apoptosis, production of a metabolite, production of another cellular product or other direct measurement of the cell. In other embodiments, the physiologic characteristic is measured indirectly such as via activation or inactivation of a reporter gene present in the cell line. In some embodiments, the toxicity of the chemical or compound is determined by measuring cellular ATP levels, mitochondrial membrane potential, plasma membrane integrity or the redox potential of the cell. In some embodiments, the gene expression of one or more reporter genes are measured to determine the biological effect of a chemical or compound. For example, a promoter-reporter assay (e.g. Estrogen Response Element (ERE)-luciferase) can be measured to determine biological activity of a compound.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Figure 2:
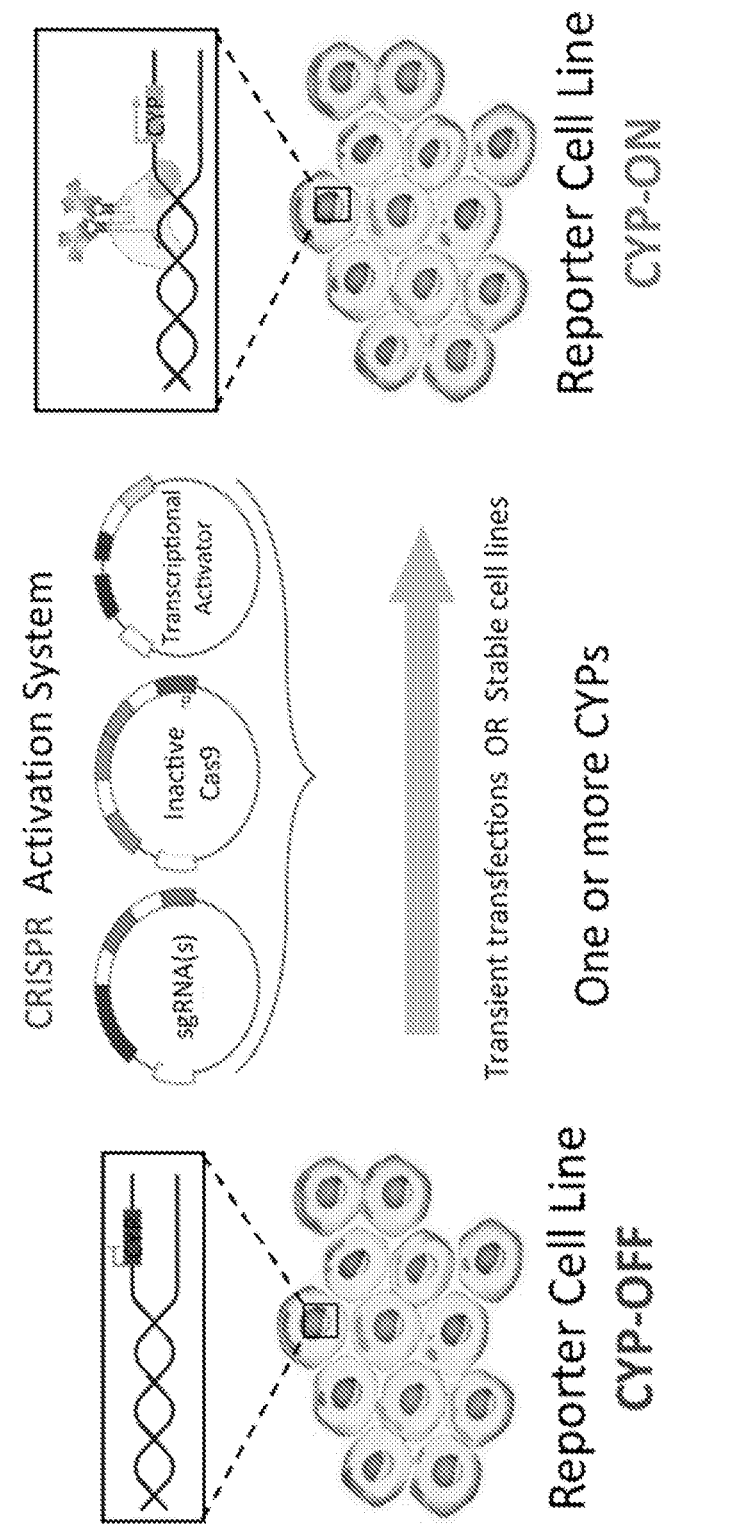
FIG. 2 shows a diagram of an approach to activate cytochrome P450 or other metabolic gene(s) in a cell line for high-throughput screening (HTS) assays. CRISPR metabolic activation of genes (C-MAGIC) components can be expressed in a reporter cell line. Targeting sgRNA(s) can be provided to the reporter cell line by expression, infection, or transfection. The targeted metabolic genes can then be expressed. Metabolic competence of modified reporter cell lines can be optionally assessed. The metabolically competent engineered cell lines can then be used in a HTS assay.

Example 1. Transient Modulation of Cytochrome P450 and Other Phase I and Phase II Metabolic Genes in Cell Lines Introduction Modulating the expression of CYP450 genes and other metabolic enzymes can affect the response to a toxic exposure. In this Example the CRISPR-Cas9 system was used to transiently activate metabolically important genes in a high throughput screening (HTS) cell-based assay. Transcriptional activation using the CRISPR-Cas9 system is an innovative approach to induce the endogenous expression of metabolic enzymes in human cell lines, particularly for development of assays capable of sensing toxic exposure and response thereto. A feature of the assay is the RNA-guided recruitment of Cas9 to specific regions of the genome. While most CRISPR-Cas9 uses inactivate a target gene, fusion of a catalytically inactive Cas9 to a transcriptional activation domain is used to activate a target gene when expressed with a sgRNA that recruits the fusion complex to the gene promoter. Multiple tools currently exist for using CRISPR-Cas9 to enhance transcription from a gene[1]. For example, one tool for transcriptional activation using CRISPR-Cas9 is the synergistic activation mediator (SAM) system[2]. The system is comprised of multiple components: Protein components of the system are a catalytically inactive Cas9 nuclease fused to a VP64 transcriptional activator (dCas9-VP64) and a co-activation complex (MS2-p65-HSF1). The third component is a RNA molecule (sgRNA) that incorporates a gene-specific 20 bp guide sequence in addition to MS2 RNA aptamers. The synergistic activation mediator (SAM) CRISPR-Cas9 system or similar system can be used to activate the expression of metabolically important genes in human cell lines used in HTS (FIGS. 1 and 2). This Example can demonstrate a metabolically competent environment for toxicity testing, and ultimately mimic tissue-specific metabolism in vitro while studying toxicity of certain chemicals.

Materials and Methods

The specific sgRNA sequences can be found in Table 2 shown in Example 2.

Figure 3:
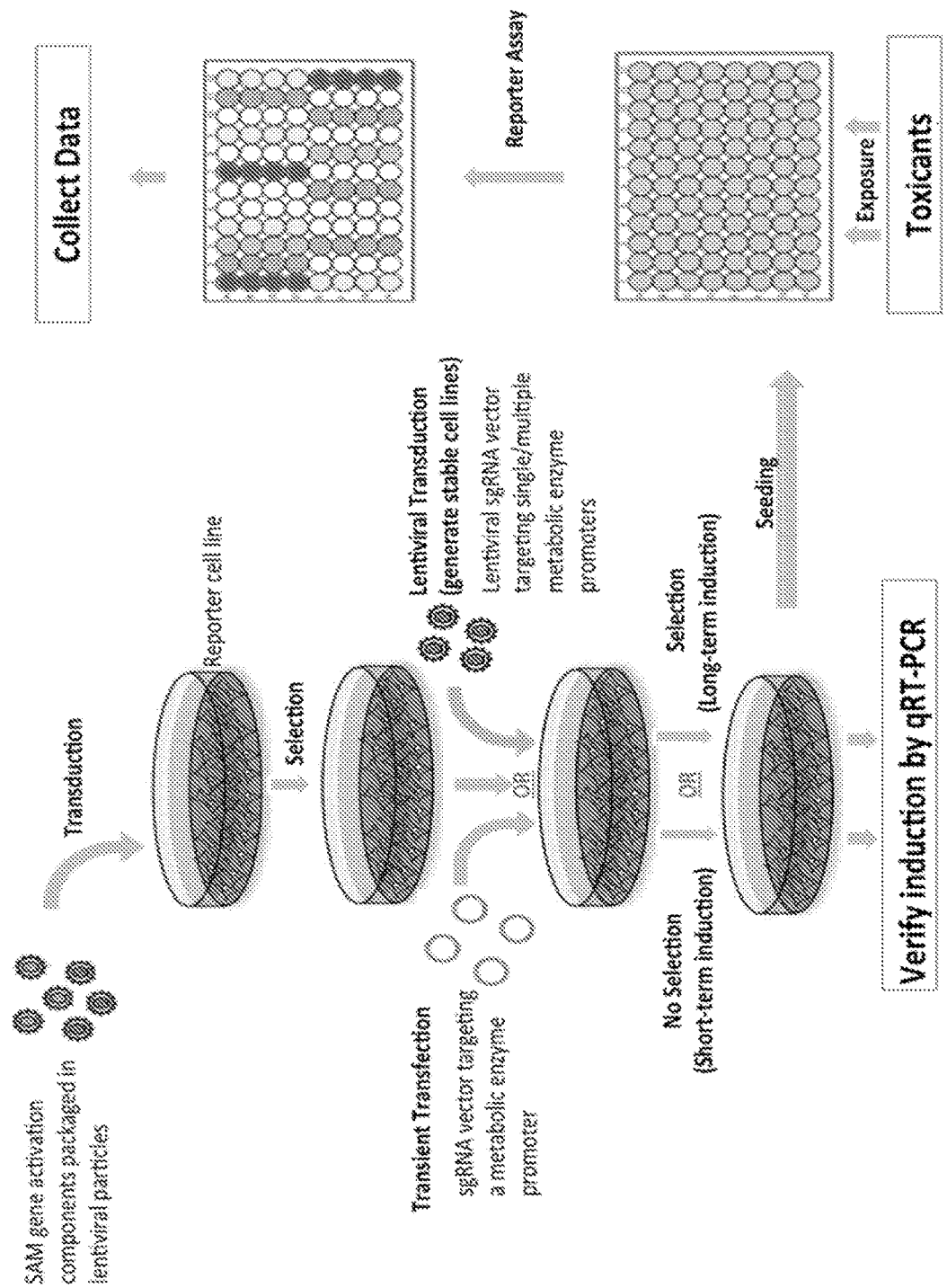
FIG. 3 shows a process flow diagram for generating and utilizing metabolically competent cells for an HTS via CRISPR based transcription activation.
Figure 4:
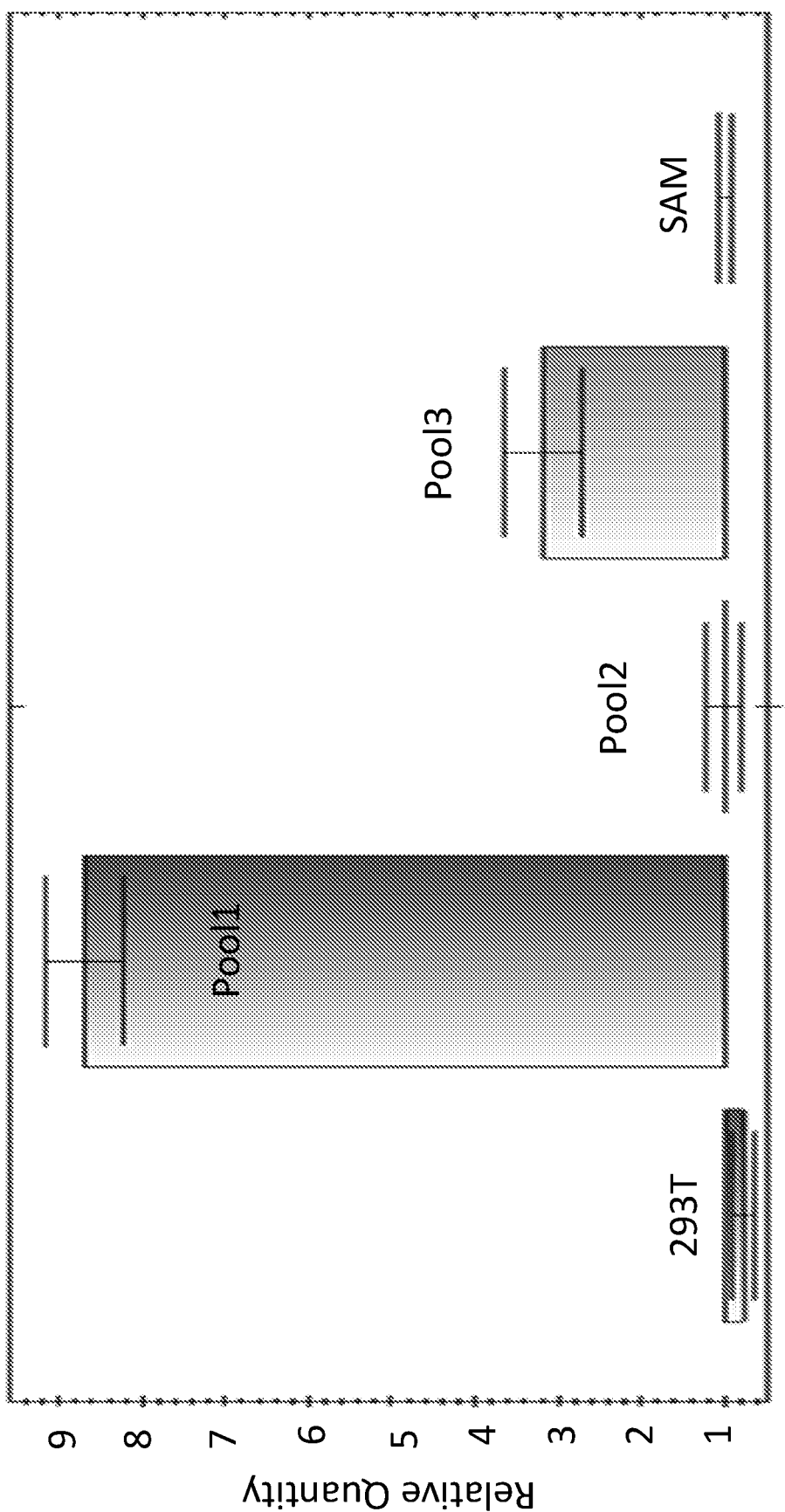
FIG. 4 shows a graph demonstrating RT-qPCR results after transient transfection for the sgRNA target of CYP1A2 and evaluation activation of gene expression of CYP1A2 and various Phase I genes including CYP3A4, CYP3A5, CYP2E1, CYP2B6. 293T refers to the HEK293T cell line control which did not receive any treatment or transfection. Pool1 refers to a transfection conducted in which sgRNAs CYP1A2, CYP2B6, CYP2E1, CYP3A4, UGT1A6, dCas9-VP64 and MS2-P65-HSF1 were pooled and administered to HEK293T cells simultaneously in a single transfection. Pool2 refers to the same pooling of the same components as Pool1, except that sgRNAs for CYP1A2, CYP2B6, CYP2E1, CYP3A4, and UGT1A6 with slightly different sequences were used. Pool3 refers to the same pooling of the same components as Pool1 and Pool2, except that sgRNAs for CYP1A2, CYP2B6, CYP2E1, CYP3A4, and UGT1A6 with slightly different sequences were used. SAM refers to a control treatment wherein the HEK293T cells were transfected with the dCas9, and MS2-p65-HSF1 plasmids, but no sgRNA plasmids for any metabolic genes.
Figure 5:
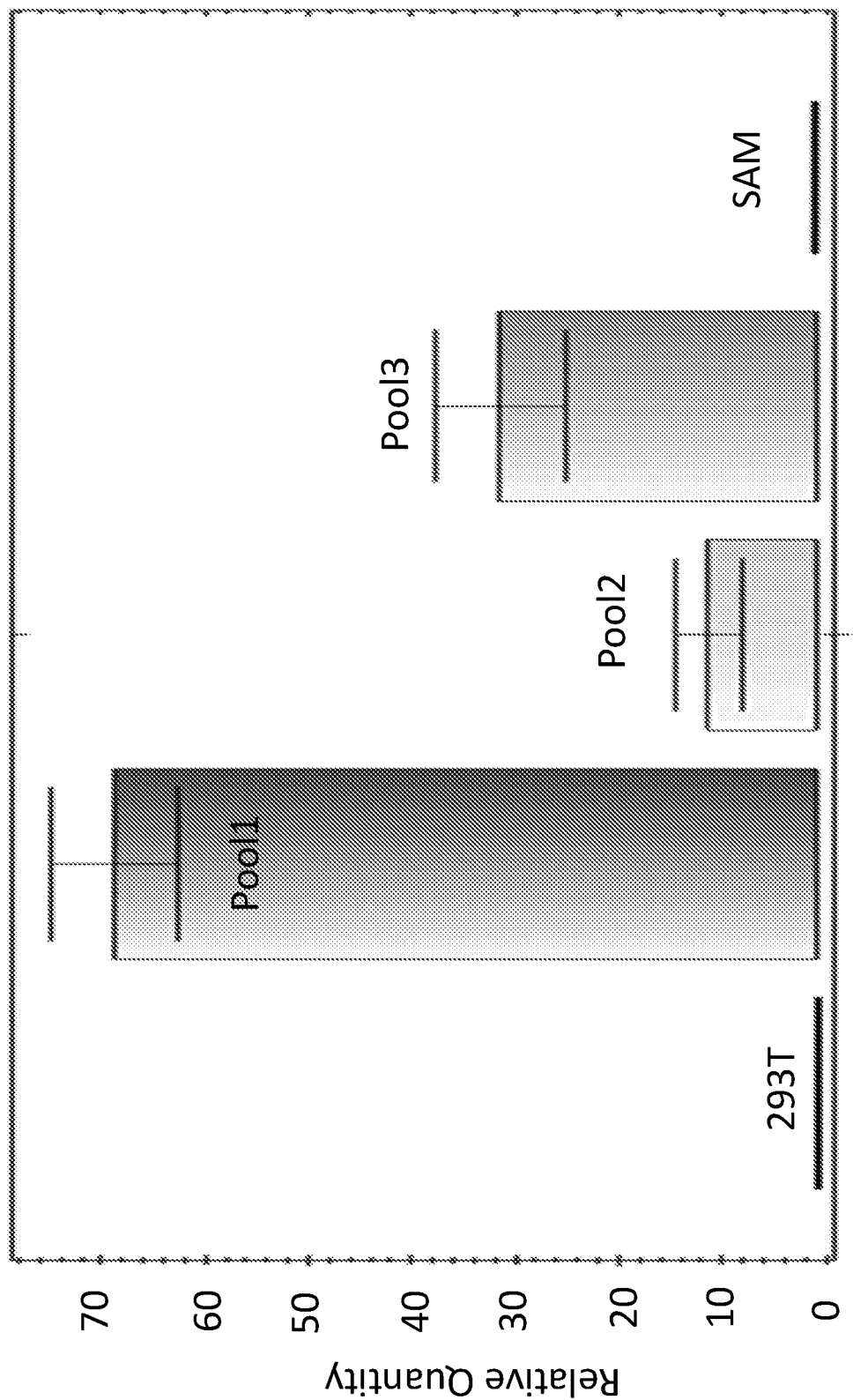
FIG. 5 shows a graph demonstrating RT-qPCR results after transient transfection for the sgRNA target of CYP3A4 and evaluation of activation of gene expression of CYP3A4 and various Phase I genes including CYP3A4, CYP3A5, CYP2E1, CYP2B6. 293T refers to the HEK293T cell line control which did not receive any treatment or transfection. Pool1 refers to a transfection conducted in which sgRNAs CYP1A2, CYP2B6, CYP2E1, CYP3A4, UGT1A6, dCas9-VP64 and MS2-P65-HSF1 were pooled and administered to HEK293T cells simultaneously in a single transfection. Pool2 refers to the same pooling of the same components as Pool1, except that sgRNAs for CYP1A2, CYP2B6, CYP2E1, CYP3A4, and UGT1A6 with slightly different sequences were used. Pool3 refers to the same pooling of the same components as Pool1 and Pool2, except that sgRNAs for CYP1A2, CYP2B6, CYP2E1, CYP3A4, and UGT1A6 with slightly different sequences were used. SAM refers to a control treatment wherein the HEK293T cells were transfected with the dCas9, and MS2-p65-HSF1 plasmids, but no sgRNA plasmids for any metabolic genes.
Figure 6:
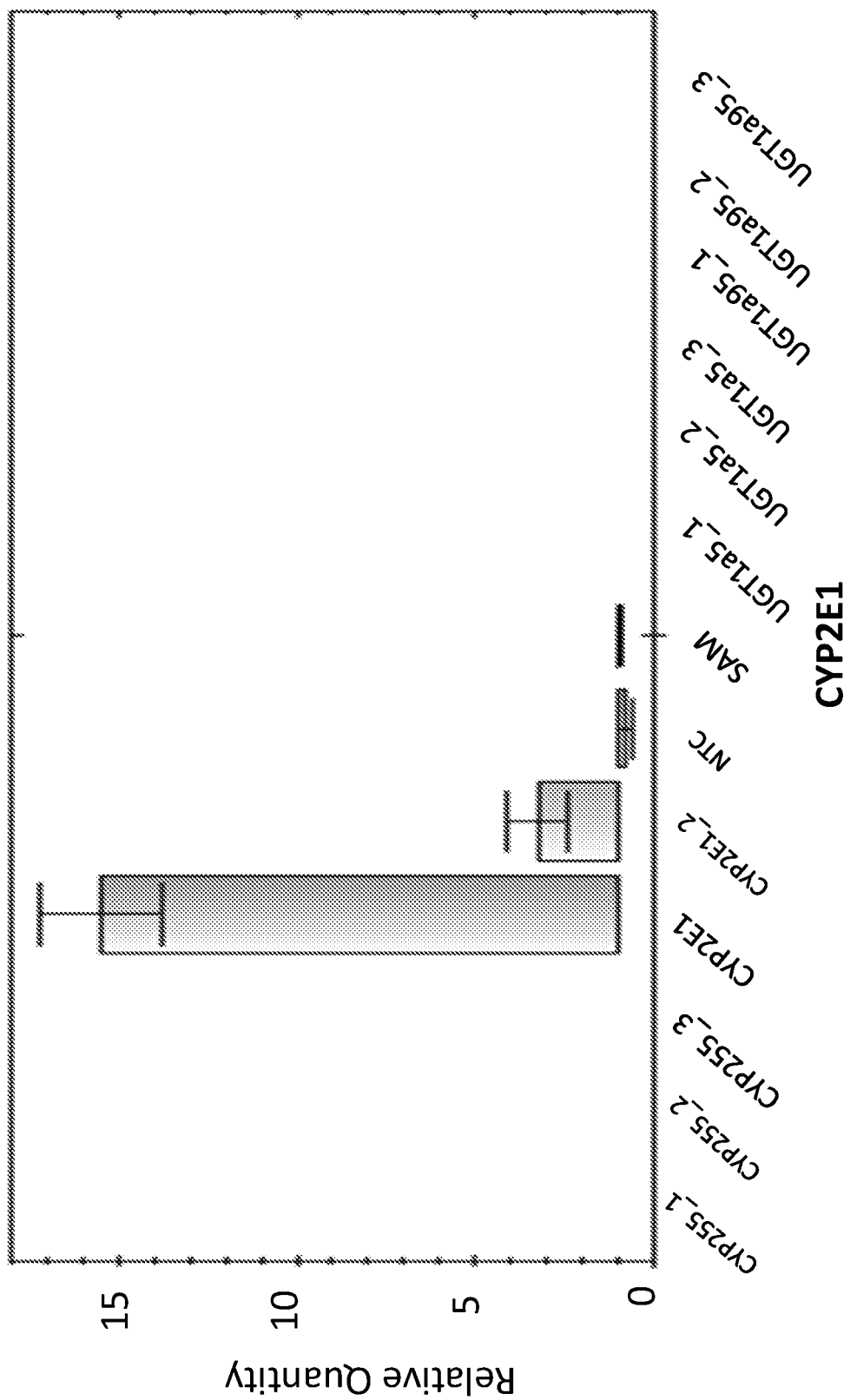
FIG. 6 shows a graph demonstrating RT-qPCR results after transient transfection for the sgRNA target of CYP2E1 and evaluation of activation of gene expression of CYP2E1 and other various Phase I and Phase II genes. In this figure, "CYP255" indicates the gene for the CYP2B6 enzyme. In this figure, "UGT1a95" indicates the gene for the UGT1a9 enzyme.
Figure 7:
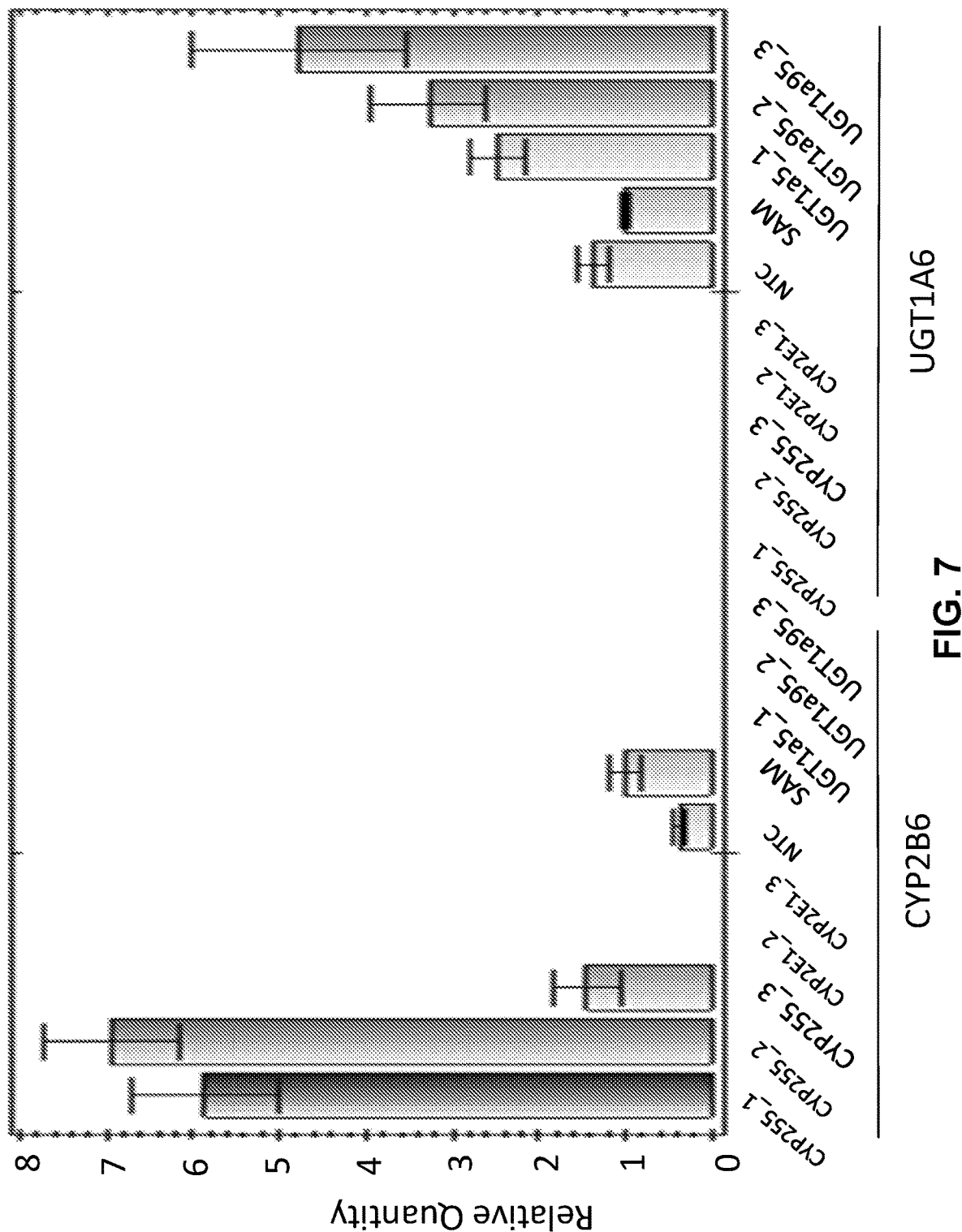
FIG. 7 shows a graph demonstrating RT-qPCR results after transient transfection for the sgRNA target of CYP2E1 and evaluation of gene expression of CYP2B6 and UGT1A6 and other Phase I genes and Phase II genes. In this figure, "CYP255" indicates the gene for the CYP2B6 enzyme. In this figure, "UGT1a95" indicates the gene for the UGT1a9 enzyme.

The overall process flow for the use of this approach in HTS is illustrated in FIG. 3. Briefly, transient transfections were used to provide the components for metabolic enzyme expression immediately prior to each HTS, which can be performed in about 30 min to 48 hours or more after transient transfection. In this study, sgRNA constructs were designed and generated to transiently active transcription of CYP1A2, CYP3A4, CYP3A5, CYP2E1, CYP2B6, UGT1a6, and UGT1a9 in HEK293 cells. It will be appreciated that constructs to transiently activate the other genes listed in Table 1 will be able to be produced by one of ordinary skill in the art without undue experimentation in view of the design and production methods demonstrated in this Example and described elsewhere herein.

More specifically, a suitable transient transfection or transduction approach using DNA/RNA transfection or virus (e.g. lentivirus) infection techniques can be used to induce transient activation of the metabolic genes of interest. Suitable transfection techniques beyond those described herein will be instantly appreciated by one of ordinary skill in the art. In this Example, each guide strand was cloned individually in the *lenti* sgRNA(MS2)_zeocin plasmid (addgene#61427) using the Golden-Gate sgRNA method described in detail in Konermann S et al. 2014[2]. After selection, bacteria were cultured flasks of liquid LB-Amp and on LB-Amp agar plates. Maxi Preps of plasmid were made from bacteria cultured in flasks of liquid LB-AMP using Qiagen Plasmid kits.

HEK293T cells were maintained in Dulbecco's Modified Eagle Medium (DMEM) with 10% (v/v) fetal bovine serum (FBS) and 1% (v/v) Penicillin/Streptomycin. The day before transfection, cells were trypsinized and counted. Cells were seeded in a 24-well at about $1.25 \times 10^5$ cells per well in about 0.5 ml of complete growth medium. Cell density was about 50-80% confluent on the day of transfection. Using a 24-well plate, about 0.5 µg of dCas9 plasmid, about 0.5 µg of SAM plasmid, and up to about 0.5 µg of sgRNA plasmid, not exceeding a total of about 1.5 µg per well for a 24-well plate, was added to a volume of Optimem equal to 50 µL for each well to be transfected. This mixture and additional reagents were prepared as directed by the Lipofectamine 3000 kit (Thermofisher Cat. L3000015). Cells were then incubated at 37° C. in a $CO_2$ incubator.

About 48 hours post-transfection, gene expression was quantified using RT-qPCR. Briefly, RNA was extracted from cells using Qiagen RNeasy Mini Kit (Cat No./ID: 74104) according to the manufacturer's instructions. RNA was quantified on Infinite 200 NanoQuant plate reader (Tecan). cDNA was synthesized using a Bio-Rad T100 Thermal Cycler and iScript™ Reverse Transcription Supermix kit (Bio-Rad 1708841) with 1 µg of RNA per sample according to the manufacturer's instructions. The cDNA was used in cDNA as the template in the qPCR experiments, which were performed using a Bio-Rad CFX Connect Real-Time System using SsoFast™ EvaGreen® Supermix (Bio-Rad 1725201). Expression data was normalized (ΔΔCq) to either GAPDH or RPL19, and we compared the fold expression of enzyme transcripts against controls receiving Cas9 and SAM components but no sgRNA plasmids.

Results. The gene expression results are demonstrated in FIGS. 4-7. In FIGS. 4-7, CYP gene expression was measured about 48 h post-transfection and is presented in terms of relative quantity of SAM-only control and normalized to expression of RPL19. Transcriptional activation of the desired genes in HEK293T cell lines using a transient transfection approach as indicated by RT-qPCR. In all cases it was observed that the CYP3A4 gene is effectively upregulated using CRISPRa. The most effective guide (sgRNA) generated about a 65-fold increased expression of CYP3A4 expression over the control when the guide was transiently transfected. However, we do not believe that this is by no means the maximum expression increase that may be achieved with our system, further refinement of sgRNA sequences or transfection techniques will likely yield increased expression beyond what we have demonstrated here.

REFERENCES FOR EXAMPLE 1

1. Du D, Qi L S. CRISPR Technology for Genome Activation and Repression in Mammalian Cells. Cold Spring Harb Protoc. 2016; 2016(1):pdb prot090175. doi: 10.1101/pdb.prot090175. PubMed PMID: 26729910.
2. Konermann S, Brigham M D, Trevino A E, Joung J, Abudayyeh O O, Barcena C, Hsu P D, Habib N, Gootenberg J S, Nishimasu H, Nureki O, Zhang F. Genome-scale transcriptional activation by an engineered CRISPR-Cas9 complex. Nature. 2015; 517(7536):583-8.

Figure 10:
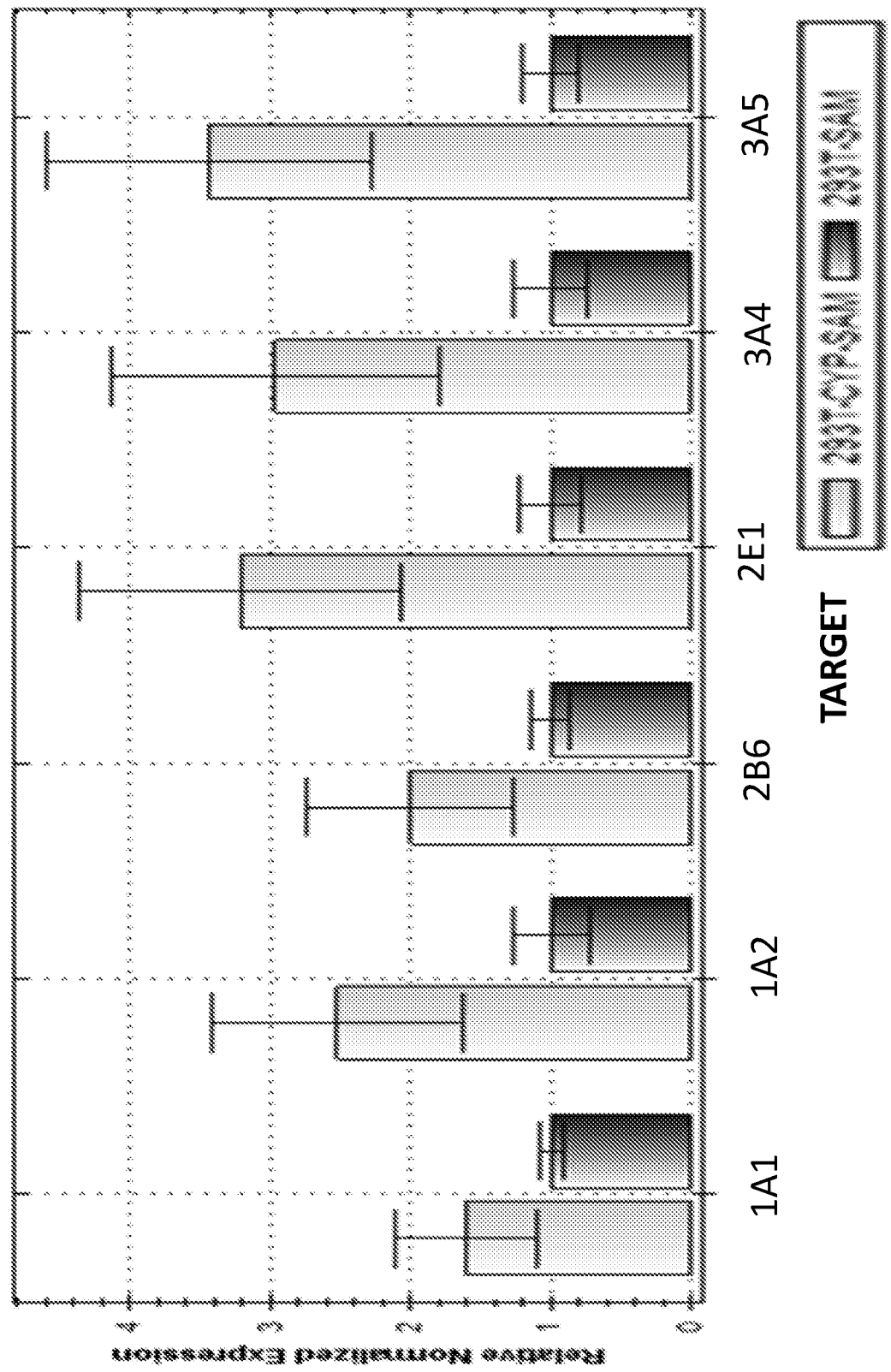
FIG. 10 shows a graph demonstrating RT qPCR results from 293T-CYP3A5/1A1/3A4 cells (a HEK293T cell line stably transfected with CYP3A4, CYP3A5, and CYP1A1) and 293T-SAM cells (a HEK293T cell line stably transfected with dCas9-VP64 and MS2-P65-HSF1), transfected with CYP2B6, CY2E1, CYP1A2.

Example 2. Stable Modulation of Cytochrome P450 and Other Phase I and Phase II Metabolic Genes in Cell Lines Modulating the expression of CYP450 genes and other metabolic enzymes can affect the response to a toxic exposure. In this Example the CRISPR-Cas9 system was used to stably activate metabolically important genes in a high throughput screening (HTS) cell-based assay, as indicated in FIG. 10. Transcriptional activation using the CRISPR-Cas9 system is an innovative approach to induce the endogenous expression of metabolic enzymes in human cell lines, particularly for development of assays capable of sensing toxic exposure and response thereto. A feature of the assay is the RNA-guided recruitment of Cas9 to specific regions of the genome. While most CRISPR-Cas9 uses inactivate a target gene, fusion of a catalytically inactive Cas9 to a transcriptional activation domain is used to activate a target gene when expressed with a sgRNA that recruits the fusion complex to the gene promoter. Multiple tools currently exist for using CRISPR-Cas9 to enhance transcription from a gene[1]. For example, one tool for transcriptional activation using CRISPR-Cas9 is the synergistic activation mediator (SAM) system[2]. The system is comprised of multiple components: Protein components of the system are a catalytically inactive Cas9 nuclease fused to a VP64 transcriptional activator (dCas9-VP64) and a co-activation complex (MS2-p65-HSF1). The third component is a RNA molecule (sgRNA) that incorporates a gene-specific 20 bp guide sequence in addition to MS2 RNA aptamers. The synergistic activation mediator (SAM) CRISPR-Cas9 system or similar system can be used to activate the expression of metabolically important genes in human cell lines used in HTS (FIGS. 1 and 2). This Example can demonstrate a metabolically competent environment for toxicity testing, and ultimately mimic tissue-specific metabolism in vitro while studying toxicity of certain chemicals.

Materials and Methods

TABLE 2

| Designation | sgRNA Sequence | SEQ ID NO: | Batch # |
|---|---|---|---|
| CYP1A1 | CTCTCTGGGATTGGAGAGAA | 1 | Batch #1 |
| | GGGTGGGCAAGAACCCACTA | 2 | |
| | AGAAGCAGCCTGAACCGGGC | 3 | |
| CYP3A4 | ACTCAAAGGAGGTCAGTGAG | 4 | |
| | TGGAAGAGGCTTCTCCACCT | 5 | |
| | TGATTCTTTGCCAACTTCCA | 6 | |
| CYP1A2 | GGATAGGCCAGAAGGGGTGC | 7 | Batch #2 |
| | TAAGACCCAGGGTGACTCTT | 8 | |
| | GAAGGATCAACTCTTGGCCT | 9 | |
| CYP2B6 | GGGATAGGCATCAGGTCACT | 10 | |
| | ATGAAAAAGGAGGTGGGGAA | 11 | |
| | GGGAACCCAGACTTCCTGCT | 12 | |
| CYP2E1 | GGAATCAGCCTTTGAAACGA | 13 | |
| | GGTTTATTATTAGCTGCTGT | 14 | |
| | AGCCAGTGACCTGGTGAGGA | 15 | |
| UGT1A6 | TTCTACACAGGTCTTGCTCT | 16 | |
| | AAGTCTGTTCTAGTAATTCA | 17 | |
| | CAGAGCTAGTCATGCACACC | 18 | |
| CYP2B6 | TATAACAGGGTGCAGAGGCA | 19 | Batch #3 |
| | GTCAGGATAAAAGGCCCAGT | 20 | |
| | GGAGGCTGCAGCAGGGTGCA | 21 | |

TABLE 2-continued

| Designation | sgRNA Sequence | SEQ ID NO: | Batch # |
|---|---|---|---|
| CYP2E1 | GCAAGAGGGCATTGGTTGGT | 22 | |
| | ACTCGTCTATCCCAAATTAC | 23 | |
| | TAAAAACCTTCCGTTTCCAC | 24 | |
| UGT1A6 | TAGGCTGTCCCAGTGAGAGG | 25 | |
| | AGCTCAGGTGAAAGCTGACA | 26 | |
| | AATTGGCAGGGGGTCCTCAG | 27 | |
| UGT1A9 | AGCTCCTATGATACAGTAGG | 28 | |
| | TTCCAGACAACAGTAGCTTA | 29 | |
| | ATTGGGGTCAGGTTTTGTGC | 30 | |

HEK293T cells stably transfected with the SAM component were generated using lentiviral transduction. Briefly, Lentiviruses were produced for each of the SAM components and packaged by co-transfecting using lipofectamine 3000 and each of the following lentiviral plasmids: addegene#61425 (dCas9-VP64), Addgene#61426 (MS2-P65-HSF1 activator helper complex), or guide RNA plasmid (addegene#61427 harboring a cloned CYP activation gRNA), with the psPAX2 packaging and pMD2. G envelope plasmids. The day after the transfection, the cell culture medium was replaced with fresh medium (DMEM, 10% FBS). After about 48 h of culture, the medium, which contained the lentivirus, was collected and then filtered using 0.45 µM sterile syringe filters. The 293T cells were seeded in 6-well plates and infected with 250 µl of the lentiviral solution in the presence of 8 µg/ml polybrene to enhance the infection rate. After about 24 h, the media was changed and the cells were allowed to grow for another 24 h before starting the selection against the appropriate antibiotics. 293T cells were transduced either with dCas9-VP64 alone to generate 293T-Cas9-VP64 (blasticin selection) or with both dCas9-VP64 and MS2-P65-HSF1 lentiviruses (blasticin and hygromycin B selection) to generate 293T-SAM.

To generate 293T-CYP3A5/1A1/3A4-SAM cells, 293T cells were co-transduced with the two previous components and with lentiviruses for three different CYP3A5 activation guides (blasticin, hygromycin B, and zeocin selection). Once the selection was completed, the successfully-transfected cells were transduced yet again with CY3A4 and CY1A1 lentiviruses (for all sgRNA guides). Transfections were performed using all three of the potential activation guides, as it was not known which guide sequences would prove to be the most effective for inducing expression in the stable-transfection cell lines. Transfections were performed sequentially to increase the likelihood of success. RT-qPCR was performed 48 hours after the final transfection.

Figure 8:
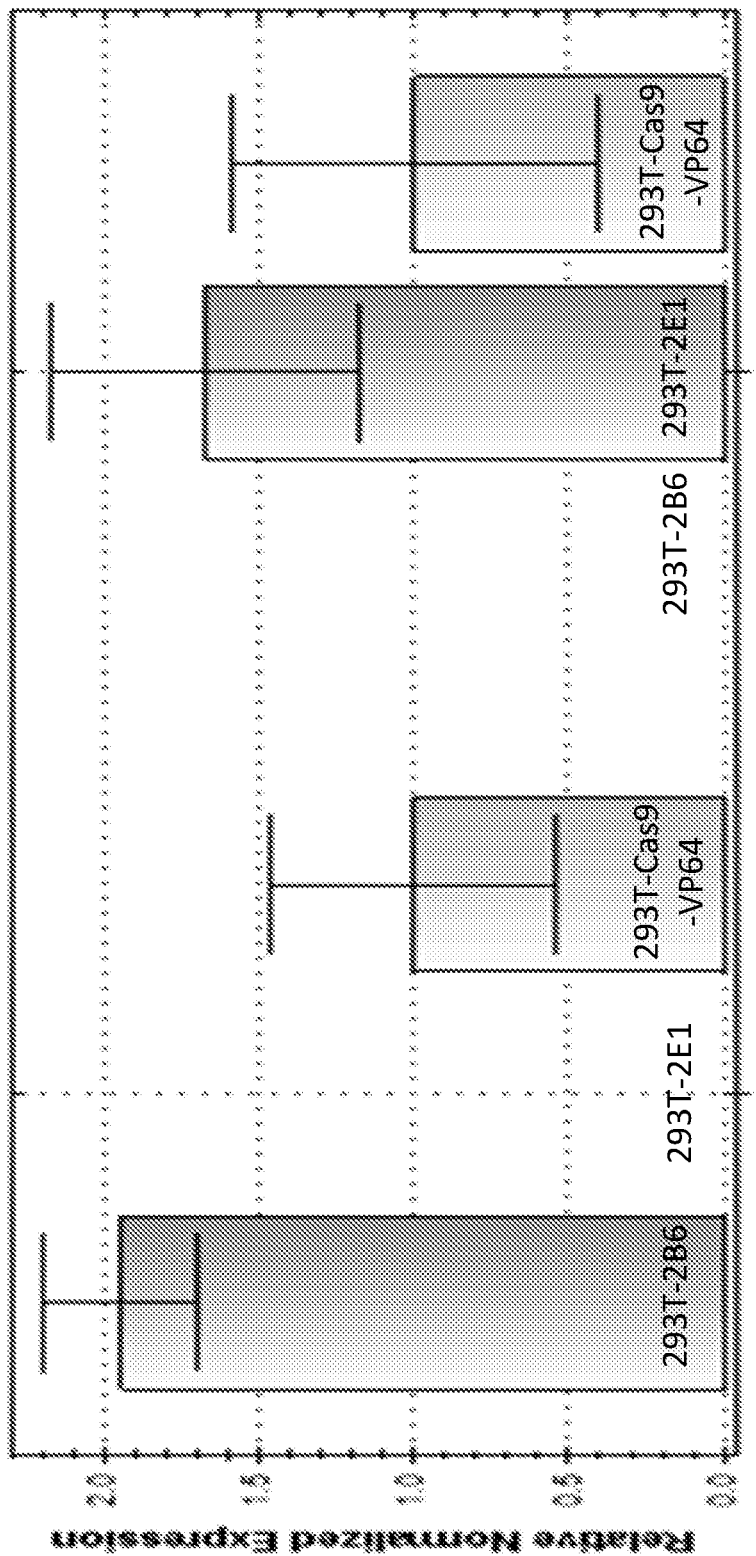
FIG. 8 shows a graph demonstrating RT-qPCR results from 293T-Cas9-vP64 cells transfected with the MS2-p65-HSF1 activator helper component and CYP2B6 or CYP2E1 sgRNA plasmids.
Figure 9:
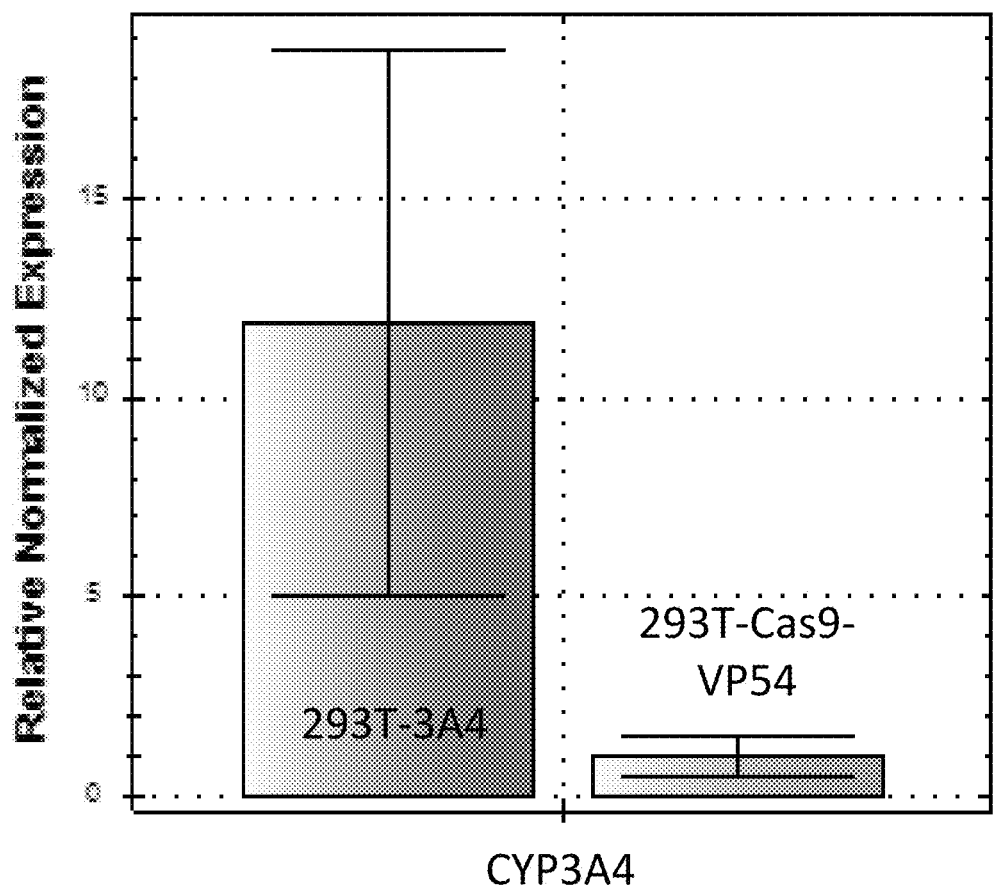
FIG. 9 shows a graph demonstrating RT-qPCR results from 293T-Cas9-vP64 cells transfected with the MS2-p65-HSF1 activator helper component and CYP3A4 sgRNA plasmid.

The results are demonstrated in FIGS. 8-10. In all cases it was observed that the CYP3A4 gene is effectively upregulated using CRISPRa. The most effective guide (sgRNA) generated about a 12-fold increase in expression (FIGS. 8-9). As demonstrated in FIGS. 8-9, the gene expression level of the CYP2B6, CYP2E1, and CYP3A4 was increased as compared to the control. As demonstrated in FIG. 10, the CYP2B6, CYP1A2, CYP2E1 as well as the CYP3A4 and CYP3A5 expression was increased in the transfected 293T-CYP3A5/1A1/3A4 cells when compared to the 293T-SAM cells.

REFERENCES FOR EXAMPLE 2

1. Du D, Qi L S. CRISPR Technology for Genome Activation and Repression in Mammalian Cells. Cold Spring Harb Protoc. 2016; 2016(1):pdb prot090175. doi: 10.1101/pdb.prot090175. PubMed PMID: 26729910.
2. Konermann S, Brigham M D, Trevino A E, Joung J, Abudayyeh O O, Barcena C, Hsu P D, Habib N, Gootenberg J S, Nishimasu H, Nureki O, Zhang F. Genome-scale transcriptional activation by an engineered CRISPR-Cas9 complex. Nature. 2015; 517(7536):583-8.

We claim:

1. A genetically engineered cell line comprising an immortalized cell line comprising:
   i) one or more modulated metabolic genes, wherein the expression of the one or more modulated metabolic genes is greater than the expression in an unmodified control cell,
      wherein the one or more modulated metabolic genes are selected from the group consisting of: CYP1A1, CYP1A2, CYP2B6, CYP2E1, and CYP3A4;
   ii) one or more sgRNAs for one or more metabolic genes, wherein the one or more sgRNAs are one or more of SEQ ID NOs: 1-15 and 19-24; and
   iii) an inactive Cas9 (dCas9) operatively linked to a VP64 transcriptional activator.

2. The genetically engineered cell of claim 1, wherein the genetically engineered cell is metabolically competent.

* * * * *